United States Patent
Vener et al.

(10) Patent No.: US 11,559,540 B2
(45) Date of Patent: Jan. 24, 2023

(54) METHOD OF DETERMINING ACUTE MYELOID LEUKEMIA RESPONSE TO TREATMENT WITH FARNESYLTRANSFERASE INHIBITORS

(71) Applicant: Janssen Pharmaceutica NV, Beerse (BE)

(72) Inventors: Tatiana I. Vener, Sterling, NJ (US); Carlo C. Derecho, Lakehurst, NJ (US); John F. Palma, Alamo, CA (US); Mical Raponi, San Francisco, CA (US)

(73) Assignee: Janssen Pharmaceutica NV, Beerse (BE)

( * ) Notice: Subject to any disclaimer, the term of this patent is extended or adjusted under 35 U.S.C. 154(b) by 552 days.

(21) Appl. No.: 13/750,258

(22) Filed: Jan. 25, 2013

(65) Prior Publication Data

US 2013/0130999 A1    May 23, 2013
US 2016/0095874 A9    Apr. 7, 2016

Related U.S. Application Data

(63) Continuation of application No. PCT/US2011/045693, filed on Jul. 28, 2011.

(60) Provisional application No. 61/368,453, filed on Jul. 28, 2010.

(51) Int. Cl.
| | |
|---|---|
| C12Q 1/68 | (2018.01) |
| A61K 31/7048 | (2006.01) |
| A61K 31/4709 | (2006.01) |
| C12Q 1/6886 | (2018.01) |

(52) U.S. Cl.
CPC ...... *A61K 31/7048* (2013.01); *A61K 31/4709* (2013.01); *C12Q 1/6886* (2013.01); *C12Q 2600/106* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,922,571 A | 7/1999 | Hillman | |
| 7,119,186 B2 * | 10/2006 | Tsuji | 536/23.1 |
| 7,932,036 B1 | 4/2011 | Raponi et al. | |
| 8,249,814 B2 | 8/2012 | Liew et al. | |
| 2004/0110792 A1 | 6/2004 | Raponi | |
| 2005/0003422 A1 | 1/2005 | Raponi | |
| 2006/0111358 A1 | 5/2006 | De Bont et al. | |
| 2007/0213939 A1 | 9/2007 | Chao et al. | |
| 2008/0280297 A1 * | 11/2008 | Dalla-Favera | 435/6 |
| 2009/0208942 A1 | 8/2009 | Liew et al. | |

FOREIGN PATENT DOCUMENTS

| | | |
|---|---|---|
| EP | 1 478 773 B1 | 11/2004 |
| EP | 1 767 656 A2 | 3/2007 |
| JP | 2005522990 A | 5/2003 |
| JP | 2006-503871 A | 2/2006 |
| JP | 2009-512440 A | 3/2009 |
| MX | PA04004072 A | 5/2003 |
| WO | 2004/032935 A1 | 4/2004 |
| WO | 2007/048074 A1 | 4/2007 |
| WO | WO 2008/112749 A1 | 9/2008 |

OTHER PUBLICATIONS

Karp et al; Blood, vol. 119, pp. 55-63, Oct. 14, 2011.*
Genbank Accession AY634315, NCBI, NLM, (2007).*
Raponi et al; Blood, Nov. 20, 2009, vol. 114, abstract 4154.*
Karp, J. E. and Lancet, J. E. Biologies: Targets & Therapy 2008, vol. 2, pp. 491-500.*
Sakhinia et al; J. Clin. Pathol. vol. 59, 2006, pp. 1059-1065.*
Cronin et al; Clinical Chemistry, vol. 50, pp. 1464-1471; 2004.*
Petersen et al; Anal. Biochem. vol. 366, pp. 46-58; 2007.*
Livak et al; Methods, vol. 25, 2001, pp. 402-408.*
Ahel et al. (2006) The neurodegenerative disease protein aprataxin resolves abortive DNA ligation intermediates Nature 443:713-716.
Baylin et al. in Nature Clinical Practice (2005) 2:S1-S3.
Bivona et al. (2003) Phospholipase Cgamma activates Ras on the Golgi apparatus by means of RasGRP1 Nature 424:694-698.
Bos (1989) ras oncogenes in human cancer: a review Cancer Res 49:4682-4689.
Bullinger et al. (2004) Use of gene-expression profiling to identify prognostic subclasses in adult acute myeloid leukemia N Engl J Med 350:1605-1616.
Burger et al. (2005) Activating mutations in c-KIT and PDGFRalpha are exclusively found in gastrointestinal stromal tumors and not in other tumors overexpressing these imatinib mesylate target genes Cancer Biol Ther 4:1270-1274.
Chang et al. (2003) Gene expression profiling for the prediction of therapeutic response to docetaxel in patients with breast cancer Lancet 362:362-369.

(Continued)

*Primary Examiner* — Jehanne S Sitton
(74) *Attorney, Agent, or Firm* — BakerHostetler

(57) ABSTRACT

The disclosed method rapidly identifies with desired accuracy AML patients, including elderly AML patients, likely to respond to treatment with a combination of a farnesyltransferase inhibitor and one or more of etoposide, teniposide, tamoxifen, sorafenib, paclitaxel, temozolomide, topotecan, trastuzumab and cisplatinum. In an embodiment, the improvements include the use of whole blood rather than the customary bone marrow sample, thus making the assay more accurate, rapid, less intrusive, less expensive as well as less painful. The method includes evaluation of a two-gene expression ratio (RASGRP1:APTX), which with a corresponding threshold, provides sufficient accuracy for predicting the response to the combination treatment. In the preferred embodiment the combination treatment combines tipifarnib (R115777, ZARNESTRA®) with etoposide. Further, the elderly AML patients identified as being likely responsive to the combination treatment with tipinifarb and etoposide have a complete recovery rate comparable to the best therapy available for younger patients.

24 Claims, 16 Drawing Sheets

Specification includes a Sequence Listing.

(56) References Cited

OTHER PUBLICATIONS

Chen et al. (2005) FLT3/ITD mutation signaling includes suppression of SHP-1 J Biol Chem 280:5361-5369.
Cox et al (2002) Farnesyltransferase inhibitors: promises and realities Curr Opin Pharmacol 2:388-393.
Ebinu et al. (1998) RasGRP, a Ras guanyl nucleotide-releasing protein with calcium- and diacylglycerol-binding motifs Science 280:1082-1086.
Ehmann et al. (2006) Detection of N-RAS and K-RAS in their active GTP-bound form in acute myeloid leukemia without activating RAS mutations Leuk Lymphoma 47:1387-1391.
End et al. (2001) Characterization of the antitumor effects of the selective farnesyl protein transferase inhibitor R115777 in vivo and in vitro Cancer Res 61:131-137.
Feldkamp et al. (2001) Isotype-specific RasGTP-levels predict the efficacy of farnesyl transferase inhibitors against human astrocytomas regardless of Ras mutational status Cancer Res 61:4425-4431.
Geman et al. (2004) Classifying gene expression profiles from pairwise mRNA comparisons Stat Appl Genet Mol Biol 3:30.
Hollerman et al. (2004) Gene-expression patterns in drug-resistant acute lymphoblastic leukemia cells and response to treatment N Engl J Med 351:533-542.
Illmer et al. (2005) Activation of the RAS pathway is predictive for a chemo sensitive phenotype of acute myelogenous leukemia blasts Clin Cancer Res 11:3217-322.
Jansen et al. (2005) Molecular classification of tamoxifen-resistant breast carcinomas by gene expression profiling J Clin Oncol 23:732-740.
Karp et al. (2001) Clinical and biologic activity of the farnesyltransferase inhibitor R115777 in adults with refractory and relapsed acute leukemias: a phase 1 clinical-laboratory correlative trial Blood 97:3361-3369.
Karp et al. Active oral regimen for elderly adults with newly diagnosed acute myelogenousleukemia: a preclinical and phase 1 trial of the farnesyltransferase inhibitor tipifamib (R115777, Zarnestra) combined with etoposide. Blood 2009, 113:4841-4852.
Kawasaki et al. (1998) A Rap guanine nucleotide exchange factor enriched highly in the basal ganglia Proc Natl Acad Sci 95:13278-13283.
Lancet et al. (2006) A phase II study of the farnesyltransferase inhibitor tipifarnib in poor-risk and elderly patients with previously untreated acute myelogenous leukemia Blood 2:2.
Leith et al. Acute Myeloid Leukemia in the Elderly: Assessment of Multidrug Resistance (MDR1) and Cytogenetics Distinguishes Biologic Subgroups With Remarkably Distinct Responses to Standard Chemotherapy. A Southwest Oncology Group Study. Blood, vol. 89, 1997: p. 3323.
Lossos et al. (2004) Prediction of survival in diffuse large B cell lymphoma based on the expression of six genes N Engl J Med 350:1828-1837.
Lubet et al. (2006) Effects of the farnesyl transferase inhibitor R115777 (Zarnestra) on mammary carcinogenesis: prevention, therapy, and role of HaRas mutations Mol Cancer Ther 5:1073-1078.
Lynch et al. (2004) Activating mutations in the epidermal growth factor receptor underlying responsiveness of non-small-cell lung cancer to gefitinib N Engl J Med 350:2129-2139.
Ma et al. (2004) A two-gene expression ratio predicts clinical outcome in breast cancer patients treated with tamoxifen Cancer Cell 5:607-616.
Mesa et al. (2006) Tipifarnib: farnesyl transferase inhibition at a crossroads Expert Rev Anticancer Ther 6:313-319.
Moroni et al. (2005) Gene copy number for epidermal growth factor receptor (EGFR) and clinical response to antiEGFR treatment in colorectal cancer: a cohort study Lancet Oncol 6:279-286.
Perez De Castro et al. (2004) A Ras activation in Jurkat T cells following low-grade stimulation of the T-cell receptor is specific to N-Ras and occurs only on the Golgi apparatus Mol Cell Biol 24:3485-3496.
Potti et al. (2006) Genomic signatures to guide the use of chemotherapeutics Nat Med 12:1294-1300.
Rao et al. (2004) Phase III Double-Blind Placebo-Controlled Study of Farnesyl Transferase Inhibitor R115777 in Patients With Refractory Advanced Colorectal Cancer J Clin Oncol 22:3950-3957.
Raponi et al. Identification of molecular predictors of response in a study of tipifarnib treatment in relapsed and refractory acute myelogenous leukemia. Clin Cancer Res. 2007; 13: 2254-2260.
Raponi et al. A 2-gene classifier for predicting response to the farnesyltransferase inhibitor tipifarnib in acute myeloid leukemia. Blood 2008, 111: 2589-2596.
Reuter et al. (2000) Targeting the Ras signaling pathway: a rational, mechanism-based treatment for hematologic malignancies? Blood 96:1655-1669.
Reuther et al. (2001) Leukemia-associated Rho guanine nucleotide exchange factor, a Dbl family protein found mutated in leukemia, causes transformation by activation of RhoA J Biol Chem 276:27145-27151.
Reuther et al. (2002) RasGRP4 is a novel Ras activator isolated from acute myeloid leukemia J Biol Chem 277:30508-30514.
Rosenwald et al. (2002) The use of molecular profiling to predict survival after chemotherapy for diffuse large-B-cell lymphoma N Engl J Med 346:1937-1947.
Rowinsky et al (1999) Ras protein farnesyltransferase: A strategic target for anticancer therapeutic development J Clin Oncol 17:3631-3652.
Sahai et al. (2002) RHO-GTPases and cancer Nat Rev Cancer 2:133-142.
Seidman et al. (2001) Weekly trastuzumab and paclitaxel therapy for metastatic breast cancer with analysis of efficacy by HER2 immunophenotype and gene amplification J Clin Oncol 19:2587-2595.
Shipp et al. (2002) Diffuse large B-cell lymphoma outcome prediction by gene-expression profiling and supervised machine learning Nat Med 8:68-74.
Solit et al. (2006) BRAF mutation predicts sensitivity to MEK inhibition Nature 439:358-362.
Sterpetti et al. (1999) Activation of the Lbc Rho exchange factor proto-oncogene by truncation of an extended C terminus that regulates transformation and targeting Mol Cell Biol 19:1334-1345.
Stone (2006) Regulation of Ras in lymphocytes: get a GRP Biochem Soc Trans 34:858-861.
Tognon et al. (1998) Regulation of RasGRP via a phorbol ester-responsive C1 domain Mol Cell Biol 18:6995-7008.
Tsao et al. (2005) Erlotinib in lung cancer—molecular and clinical predictors of outcome N Engl J Med 353:133-144.
Van Cutsem et al. (2004) Phase III trial of gemcitabine plus tipifarnib compared with gemcitabine plus placebo in advanced pancreatic cancer J Clin Oncol 22:1430-1438.
Watters et al. (2006) Developing gene expression signatures of pathway deregulation in tumors Mol Cancer Ther 5:2444-2449.
Weinstein et al. (2006) Mechanisms of disease: Oncogene addiction—a rationale for molecular targeting in cancer therapy Nat Clin Pract Oncol 3:448-457.
Whyte et al. (1997) K- and N-Ras are geranylgeranylated in cells treated with farnesyl protein transferase inhibitors J Biol Chem 272:14459-14464.
Yeoh et al. (2002) Classification, subtype discovery, and prediction of outcome in pediatric acute lymphoblastic leukemia by gene expression profiling Cancer Cell 1:133-143.
International Search Report PCT/US 11/45693 dated Mar. 8, 2012.
Bacher, et al., Briefings in Functional Genomics and Proteomics Advance Access, Perspectives of gene expression profiling for diagnosis and therapy in haematological malignancies, May 27, 2009, pp. 1-10.
Harousseau, et al., BLOOD, A randomized phase 3 study of tipifarnib compared with best supportive care, including hydroxyurea, in the treatment of newly diagnosed acute myeloid leukemia in patients 70 years or older, 2009, vol. 114, No. 6, pp. 1166-1173.
Karp, et al., BLOOD, Active Oral Regimen for Elderly Adults with Newly Diagnosed Acute Myelogenous Leukemia (AML): Phase I Trial of Oral Tipifarnib (T) Combined with Oral Etoposide (E) for Adults =Age 70 Who Are Not Candidates for Traditional Cytotoxic Chemotherapy (TCC), 2006, 5 pages.

(56) References Cited

OTHER PUBLICATIONS

Karp, et al., History of Changes for Study: NCT00112853 Tipifarnib and Etoposide in Treating Older Patients With Newly Diagnosed Acute Myeloid Leukemia, 2010, pp. 1-10.

Livak, et al., METHODS, Analysis of Relative Gene Expression Data Using Real-Time Quantitative PCR and the 2-??CT Method, 2001, pp. 402-408.

Martinelli, et al., Journal of Clinical, Correlation of RASGRP1/APTX ratio with clinical response and survival in AML patients treated with tipifarnibbortezomib combination, 2010, Suppl 6550, pp. 1-5.

Papayannidis, et al., Cancer Research, Abstract #743: RASGRP1/APTX ratio is a strong biomarker which predicts response to therapy with Tipifarnib plus Bortezomib in elderly patients with Acute Myeloid Leukemia (AML), 2009, pp. 1-5.

Rolland, et al., Cancer Chemother Pharmacol, Phase II trial and prediction of response of single agent tipifarnib in patients with relapsed/refractory mantle cell lymphoma: a Groupe d'Etude des Lymphomes de l'Adult trial, 2009, 65 pp. 781-790.

Akoben, Anthony: Review Article, Understanding diagnostic tests 3: receiver operating characteristic curves, Acta Paediatrica, 2007, vol. 96, No. 5, 644-647.

Miyake, Kazunori: Early Diagnosis and Clinical Testing, Journal of the Japanese Society of Internal Medicine, 2005, vol. 94, No. 12, pp. 2467-2472.

Nippon Suisan Gakkaishi, Special feature: Real-time monitoring of marine microorganisms, Principles and applications of real-time quantitative PCR, 2007, vol. 37, No. 2, pp. 292-295.

\* cited by examiner

A

| | PD | R | |
|---|---|---|---|
| False | 12 | 2 | 14 |
| True | 1 | 11 | 12 |
| | 13 | 13 | 26 |

Sensitivity=84.6%
Specificity=92.3%
NPV=85.7%
PPV=91.7%
Prevalence=50%

C

| | PD | R | |
|---|---|---|---|
| False | 23 | 2 | 25 |
| True | 21 | 8 | 29 |
| | 44 | 10 | 54 |

Sensitivity=80%
Specificity=52.3%
NPV=92%
PPV=27.6%
Prevalence=18.5%
Odds ratio =4.38%

B

D

A

|       | PD | R  |    |
|-------|----|----|----|
| False | 24 | 3  | 27 |
| True  | 20 | 7  | 27 |
|       | 44 | 10 | 54 |

Sensitivity=70%
Specificity=54.5%
NPV=88.9%
PPV=25.9%
Prevalence=18.5%

2-Gene qPCR Assay Does Not Predict Response in Non-FTI-Treated AML

23 AcDVP16 (median age= 39, 23-66), 61% CR
18 FLAM (median age= 64, 42-71), 61% CR
Bone marrow samples only, Judy Karp
qPCR Assay
ROC AUC= 0.54, No predictive value
for enriching responders

SEQUENCE LISTING

```
<160> NUMBER OF SEQ ID NOS: 12

<210> SEQ ID NO 1
<211> LENGTH: 79
<212> TYPE: DNA
<213> ORGANISM: Artificial Sequence
<220> FEATURE:
<223> OTHER INFORMATION: RASGRP1 Amplicon

<400> SEQUENCE: 1
```

```
ctggacgatc tcattgacag ctgcattcaa tcttttgatg cagatggaaa cctgtgtcga    60
agtaaccaac tgttgcaag                                                 79
```

<210> SEQ ID NO 2
<211> LENGTH: 78
<212> TYPE: DNA
<213> ORGANISM: Artificial Sequence
<220> FEATURE:
<223> OTHER INFORMATION: APTX Amplicon

<400> SEQUENCE: 2

```
cgcttccgat tgggctacca cgccattccg agtatgagcc atgtacatct tcatgtgatc    60
agccaggatt ttgattct                                                  78
```

<210> SEQ ID NO 3
<211> LENGTH: 18
<212> TYPE: DNA
<213> ORGANISM: Artificial Sequence
<220> FEATURE:
<223> OTHER INFORMATION: APTX Upper Primer

<400> SEQUENCE: 3

```
cgcttccgat tgggctac                                                  18
```

<210> SEQ ID NO 4
<211> LENGTH: 22
<212> TYPE: DNA
<213> ORGANISM: Artificial Sequence
<220> FEATURE:
<223> OTHER INFORMATION: APTX Lower Primer

<400> SEQUENCE: 4

```
agaatcaaaa tcctggctga tc                                             22
```

<210> SEQ ID NO 5
<211> LENGTH: 21
<212> TYPE: DNA
<213> ORGANISM: Artificial Sequence
<220> FEATURE:
<223> OTHER INFORMATION: RASGRP1 Upper Primer

<400> SEQUENCE: 5

```
ctggacgatc tcattgacag c                                              21
```

<210> SEQ ID NO 6
<211> LENGTH: 22
<212> TYPE: DNA
<213> ORGANISM: Artificial Sequence
<220> FEATURE:
<223> OTHER INFORMATION: RASGRP1 Lower Primer

<400> SEQUENCE: 6

```
cttgcaacag ttggttactt cg                                             22
```

<210> SEQ ID NO 7
<211> LENGTH: 67
<212> TYPE: DNA
<213> ORGANISM: Artificial Sequence
<220> FEATURE:
<223> OTHER INFORMATION: HMBS Amplicon

<400> SEQUENCE: 7

```
cctgcccact gtgcttcctc ctggcttcac catcggagcc atctgcaagc gggaaaaccc    60
```

-continued

```
tcatgat                                                              67

<210> SEQ ID NO 8
<211> LENGTH: 19
<212> TYPE: DNA
<213> ORGANISM: Artificial Sequence
<220> FEATURE:
<223> OTHER INFORMATION: HMBS Upper Primer

<400> SEQUENCE: 8
cctgcccact gtgcttcct                                                 19

<210> SEQ ID NO 9
<211> LENGTH: 20
<212> TYPE: DNA
<213> ORGANISM: Artificial Sequence
<220> FEATURE:
<223> OTHER INFORMATION: HMBS Lower Primer

<400> SEQUENCE: 9
atcatgaggg ttttcccgct                                                20

<210> SEQ ID NO 10
<211> LENGTH: 31
<212> TYPE: DNA
<213> ORGANISM: Artificial Sequence
<220> FEATURE:
<223> OTHER INFORMATION: RASGRP1 TAQMAN Probe

<400> SEQUENCE: 10
cattcaatct tttgatgcag atggaaacct g                                   31

<210> SEQ ID NO 11
<211> LENGTH: 28
<212> TYPE: DNA
<213> ORGANISM: Artificial Sequence
<220> FEATURE:
<223> OTHER INFORMATION: APTX TAQMAN Probe

<400> SEQUENCE: 11
cacgccattc cgagtatgag ccatgtac                                       28

<210> SEQ ID NO 12
<211> LENGTH: 24
<212> TYPE: DNA
<213> ORGANISM: Artificial Sequence
<220> FEATURE:
<223> OTHER INFORMATION: HMBS TAQMAN Probe

<400> SEQUENCE: 12
gcttcaccat cggagccatc tgca                                           24
```

METHOD OF DETERMINING ACUTE MYELOID LEUKEMIA RESPONSE TO TREATMENT WITH FARNESYLTRANSFERASE INHIBITORS

CROSS-REFERENCE TO RELATED APPLICATIONS

This application is a continuation of PCT/US2011/045693 filed Jul. 28, 2011, which claims benefit of and priority to U.S. Provisional Application 61/368,453, filed Jul. 28, 2010.

SEQUENCE LISTING

The instant application contains a Sequence Listing which has been submitted electronically in ASCII format and is hereby incorporated by reference in its entirety. Said ASCII copy, created on Jun. 8, 2015, is named Sequence_Listing_CRF_103693-000737 and is 2,883 bytes in size.

BACKGROUND

Acute Mylogenous Leukemia ("AML") has a low prevalence in the US at about 50,000 patients, which is believed to be well below the 200,000 patients required for being labeled as an orphan disease. The prevalence of AML is greater in older patients, in whom the disease also tends to be far more difficult to treat. Elderly patients, typically defined as being at least 60 years old (although some classifications require patients to be above at least 65 or even 70 years old), succumb to the disease at a far higher rate. Response (to treatment) rates and survival in elderly AML patients average 30% to 50% for a complete recovery with a median relapse-free survival (RFS) of only about 9 to 12 months. Very few elderly patients survive beyond 2 years.

Managing the treatment of elderly AML patients presents many challenges. Although about seventy percent (70%) of patients achieve remission of AML with conventional induction therapy, because of the toxic effects of the therapy and extremely poor outcome in elderly patients, conventional induction therapy is often not offered to the elderly. The treatment options for elderly patients, then, are often little more than investigational treatments or palliative care. Nevertheless, it is possible to identify sub-groups of elderly patients that are likely to respond to conventional induction therapy. For instance, elderly patients with favorable cytogenetics and without elevated multiple drug resistance protein (MDR1) expression respond well to induction therapy. However, delay in identifying such patients resulting in a delay in the initiation of induction therapy, for instance, while waiting for results of the cytogenetic evaluation—which may take a week or so to be completed—has a markedly deleterious effect on the prognosis. Other markers of poor response include the presence of the FLT3/ITD mutation, or the expression of the CD34 antigen. Thus, effective management of elderly AML patients' treatment requires quick decisions, which, in turn, requires rapid assays to select the appropriate treatment. Some patients respond well to treatment while others decline and suffer from the side-effects.

AML patients may also be divided into those having relapsed/refractory disease and those with newly diagnosed disease. A relapsed or refractory disease state patient has either become non-responsive to treatment or the disease has returned. Either relapsed or refractory state is associated with poor prognosis.

Unfortunately the initial success of many AML treatments is often followed by relapses. Further, most treatments are not known to be effective in all patients and partial remission is largely ineffective in prolonging survival.

Farnesyl transferase inhibitors (FTIs) offer an alternative treatment even in elderly patients. Farnesyl transferase inhibitors (FTIs) inhibit the covalent attachment of the carbon farnesyl moieties to the C-terminal CAAX motif of various proteins. FTIs, significantly, appear to be better tolerated by elderly patients than conventional induction therapy. But, only about 15% to 25% of the patients respond to treatment with a farnesyl transferase inhibitor. Farnesyltransferase inhibitors, such as Tipifarnib, function by competitively inhibiting the addition of a farnesyl moiety to signaling molecules such as RAS that are implicated in cancers. Such inhibition is expected to hamper their function. Many FTIs of interest for this disclosure are described in US Patent Publication 20030050323.

Tipifarnib, also referred to as R115777 or its trade name ZARNESTRA™, the first farnesyltransferase inhibitor (FTI) to be tested in the clinic, has shown promise for treating many diseases. It has demonstrated significant activity in hematological disorders including AML, multiple myeloma (MM), Myelodysplastic Syndrome (MDS), juvenile myelomonocytic leukemia (JMML), myelofibrosis with myeloid metaplasia (MMM) and chronic myelogenous leukemia (CML), with complete response rates in AML and MDS of up to approximately 15%. Moreover, Tipifarnib often acts synergistically with other treatments. This synergy often provides an elderly patient with few other options, the ability to undergo treatment with a farnesyl inhibitor in combination with another agent while having tolerable side-effects and superior outcomes than with treatment just one agent in isolation. Notably, prior clinical trials of tipifarnib by itself did not lead to noticeable increase in survival, and some combinations with other agents, such as Cytarabine (ara-C') may even have increased mortality. The combination of tipifarnib with etoposide appears to overcome such drawbacks.

The preferred FTI, tipifarnib, inhibits the growth of many tumors/cell lines. In particular, cell lines expressing N-ras or H-ras mutations exhibit significant inhibition of cell proliferation. However, only about half of cell lines with K-ras mutations, when tested, were inhibited by FTI R115777 and then too at much higher doses. FTI R115777 also exhibited synergy with many agents in inhibiting the growth of tumors/cell lines. Notably, some cancers and other proliferative disorders are characterized by mutations in or sensitivity to different types of ras mutations. Accordingly, FTIs, including R115777, are not expected to be equally efficacious in treating all types of cancers and proliferative disorders. Indeed, where K-ras plays an important role, FTIs are unlikely to be as effective as when only N-ras or H-ras have an important role.

Another set of alternative treatments to conventional induction therapy are based on Podophyllotoxin and are described in US Patent Publication US20030050323. Podophyllotoxin is extracted from the mandrake plant. It is the parent compound from which two glycosides have been developed which compounds show significant therapeutic activity in several human neoplasms, including pediatric leukemia, small cell carcinomas of the lung, testicular tumors, Hodgkin's disease, and large cell lymphomas. These derivatives are etoposide (VP-16) which has the chemical name 4'-demethylepipodophyllotoxin-9-[4,6-0-(R)-ethylidene-beta-D-glucopyranoside] and teniposide (VM-26) which has the chemical name 4'-demethylepipodophyllotoxin-9-[4,6-0-(R)-thenylidene-beta-Dglycopyranoside].

These compounds' mechanisms of action involves the induction of DNA strand breaks by an interaction with DNA topoisomerase II or the formation of free radicals. Both etoposide and teniposide, however, cause toxic side-effects especially myelosuppression.

To increase the inhibitory efficacy of anti-tumor podophyllotoxin derivatives against tumor growth and also to provide a means for the use of lower dosages of anti-tumor podophyllotoxin derivatives, synergistic combinations with other treatments have been explored. FTIs, and in particular, tipifarnib, exhibit synergies with etoposide, which allows less toxic effective doses—a significant consideration in elderly AML patients.

The side-effects from a combination of tipifarnib and a derivative of Podophyllotoxin, such as an etoposide, are more tolerable. However, unlike the seventy percent (70%) response rate in younger AML patients, the response rate to a combination of etoposide and tipifarnib typically ranges from about 15% to 25%. Since not all AML patients respond to treatment with FTIs, it is not desirable to treat a patient with FTI if the patient is unlikely to respond, which presents a challenge prior to administering the FTI.

Although the preferred FTI, R115777, has been effective in combination therapy, it has not been possible to reliably predict such synergy between R115777 and other agents in a particular patient, in part because the extent of inhibition of farnesyl transferase activity does not correlate well with clinical changes. For instance, the mutation status of the RAS gene was considered to be a candidate biomarker for patient response to FTIs. This rationale was based on pre-clinical evidence that specific point mutations within the RAS genes cause constitutive activation of the RAS Pathway in many cancers. It is generally accepted that with tumors heavily reliant on the activation of one or two pathways, patients with such tumors should respond to drugs that inhibit those pathways. However, sometimes many pathways can be activated by multiple events and it has been found that RAS can be up-regulated in the absence of activating RAS mutations. Furthermore, no correlation between RAS mutations and response to FTIs has been demonstrated in clinical studies as has been pointed out in US Patent Publication 20070048782, which is incorporated by reference herein in its entirety. Indeed, while several early clinical studies of FTIs focused on cancers that exhibited high frequencies of RAS mutations, the response rate was disappointingly low in those trials. Thus, the problem of predicting the response of a particular patient to farnesyl transferase inhibitors in combination with other treatments awaits a suitable diagnostic assay that is rapid, accurate and affordable to make the prediction ability clinically useful.

SUMMARY

This disclosure identifies markers that predict response to treatment with a combination of a farnesyl transferase inhibitor and an etoposide. These markers enable identification of an oncology therapy with a low response profile that is not withheld from potential responders while avoiding subjecting likely non-responders to undesirable side-effects.

The preferred embodiments allow reliably and rapidly predicting if a particular patient is likely to respond to an FTI combination treatment, which treatment includes an FTI with one or more of etoposide, teniposide, tamoxifen, sorafenib, paclitaxel, temozolomide, topotecan, trastuzumab and cisplatinum. A preferred FTI combination treatment comprises tipifarnib with etoposide. Further, this disclosure meets the need to select the most effective treatment among many possible treatments, and to switch to a more effective treatment. One of the goals of treating AML, with its multiple causes, complications and treatments, is to timely and accurately predict the effectiveness of a particular treatment in a patient, especially if the patient is elderly. The disclosed personalized predictions of likely response to FTI combination treatments should allow the potentially non-responsive patients to be offered alternative treatments while treating likely responders with FTI combination treatments.

Preferred treatments include, tipifarnib, which is an orally available, nonpeptidomimetic farnesyltransferase inhibitor with demonstrated complete recovery rates in AML and MDS of up to 15% in myeloid malignancies including in elderly adults with AML who are not candidates for traditional cytotoxic therapy. Tipifarnib is also effective in high-risk myelodysplasia, and myeloproliferative disorders including agnogenic myeloid metaplasia and imatinib resistant chronic myelogenous leukemia. Significant improvements in this response rate are desirable to avoid dosing patients with tipifarnib who are highly likely to be non-responsive to it.

The method, for identifying whether a subject diagnosed with a myeloid disorder is a candidate for FTI combination treatment, comprises administering a first assay having a first outcome. If this outcome, or the reciprocal of this outcome, is less than a predetermined threshold, then the subject is flagged as unlikely to be aided by a first group of treatments, each of which requires administration of a farnesyl transferase inhibitor in combination with an agent selected from the group consisting of etoposide, teniposide, tamoxifen, sorafenib, paclitaxel, temozolomide, topotecan, trastuzumab and cisplatinum. If the subject is not flagged, then a treatment from the group of treatments is selected for administration to the subject.

The choice of the predetermined threshold is preferably such that the subject is flagged if there is a high negative predictive value for benefit from a treatment selected from the group of treatments to avoid denying effective treatment to as large a group as may be reasonable. Thus, effectively the high negative predictive value requires flagging subjects least likely to be aided by treatment with the farnesyl transferase inhibitor in combination with another agent. It should be noted that flagging a subject may be either a positive act—determining that the subject will likely benefit from a treatment—or a negative act—determining that the subject will not benefit from a treatment. Thus, flagging should also be understood as identifying a group or even defining a group.

Alternatively, the choice of the predetermined threshold can be such that the subject is flagged if there is a high positive predictive value for benefit from a treatment selected from the group of treatments to improve the likelihood of benefit from the treatment. This typically will be favored if there are many competing treatments available that can be distinguished from each other.

Further, even for subjects identified as likely to benefit from a treatment selected from the group of treatments, the treatment is selected based on a relative positive predictive value of the treatment—preferably relative to other treatments in the group. In a preferred embodiment, the myeloid disorder is acute myeloid leukemia.

In another aspect, the disclosed method may also be used to identify whether, in response to detecting a reduction in a subject's response to a past treatment, the subject should be switched over to a different future treatment. The different treatments may include a palliative treatment. Alternatively, the different treatment may comprise a different combination of an FTI with a medication like etoposide, tamoxifen, sorafenib, paclitaxel, Temozolomide, Topotecan, Trastuzumab and cisplatinum.

A positive predictive value of a treatment with a Farnesyl transferase inhibitor in combination with another agent is determined based on a fraction of subjects expected to exhibit a positive response to the treatment, wherein the positive response comprises complete remission, wherein, further, complete remission is defined by the presence of less than 5% myeloblasts with normal maturation of all cell lines, an ANC of at least 1000/μL and a platelet count of at least 100,000/μL, absence of blasts in peripheral blood, absence of identifiable leukemic cells in the bone marrow, clearance of disease-associated cytogenetic abnormalities, and clearance of any previously existing extramedullary disease.

In addition, in a preferred embodiment, the positive response further includes partial remission, wherein partial remission is defined by presence of trilineage hematopoiesis in the bone marrow with recovery of ANC and platelets to the above stated levels, but with 5 to 25% bone marrow blasts, and at least 50% decrease in bone marrow blast percentage from baseline. Further, in another preferred embodiment, the positive response further includes hematologic improvement. Hematologic improvement is defined by at least a 50% decrease in marrow blasts or decrease in any measurable extramedullary disease, recovery of ANC to 500 to 1000/μL, platelet count to 20,000 to 100,000/μL, or improvement in transfusion requirements.

In a preferred embodiment of the disclosed method a level of expression of genes RASGPR1 and APTX is estimated using a polymerase chain reaction (PCR). The PCR reactions may be performed in a single tube together with a reference PCR reaction. The sample for such amplification may be one or more of (i) a bone marrow sample; and/or (ii) a blood sample. The ratio of the expression levels of two markers, RASGRP1 and APTX, may be estimated using an external normalization control. In a preferred embodiment, amplification of amplicons comprising CTGGACGATCT-CATTGACAGCTGCATTCAATCTTTTGATGCAGATG-GAAACCT GTGTCGAAGTAACCAACTGTTGCAAG SEQ ID NO: 1 for RASGRP1 and CGCTTCCGATTGGGC-TACCACGCCATTCCGAGTATGAGCCATGTA-CATCTTCA TGTGATCAGCCAGGATTTTGATTCT SEQ ID NO: 2 for APTX is undertaken using the primer pairs selected from the group consisting of

```
                                         SEQ ID NO: 3
(i)    5'-CGCTTCCGATTGGGCTAC-3' APTX upper primer SEQ ID NO: 4
(ii)   5'- AGAATCAAAATCCTGGCTGATC-3' APTX lower primer, SEQ ID NO: 5
(iii)  5'-CTGGACGATCTCATTGACAGC-3' RASGPR1, upper primer,
and
                                         SEQ ID NO: 6
(iv)   5'-CTTGCAACAGTTGGTTACTTCG-3' RASGPR1, lower primer.
```

The performance and utility of two-gene expression ratio (RASGRP1:APTX) in predicting a clinically meaningful response to FTIs like R115777, RASGRP1 and APTX was identified by studying bone marrow from older adults with previously untreated, poor-risk acute myeloid leukemia (AML) for N-RAS mutations using global gene expression, and/or quantitative PCR (qPCR) of specific genes. Microarray profiling identified a two-gene expression ratio (RASGRP1:APTX) as providing the greatest accuracy for predicting response to tipifarnib. This classifier predicted response to tipifarnib in patients with relapsed or refractory AML, with a negative predictive value and positive predictive value of 92% and 28% respectively (odds ratio of 4.4). Therefore, in both newly diagnosed and relapsed or refractory AML, this classifier improves the overall response rate by approximately 50% while maintaining a high NPV, and significantly improves patient overall survival. The two-gene classifier may be implemented with the aid of qPCR, using which in a study a negative predictive value (NPV) and positive predictive value (PPV) of 81% and 50% respectively (odds ratio of 4.3) were observed. Such data indicate that a simple two-gene expression assay can be used to identify AML patients who are likely to respond to tipifarnib (R115777). Further, the two-gene assay may be used not only in newly diagnosed patients, but also in those exhibiting refractory or relapsed AML, for instance following induction therapy, and for providing maintenance therapy.

In an exemplary embodiment, a rapid two-gene ratio RASGRP1:APTX is determined by the steps of collecting a peripheral whole blood sample, isolating the RNA from the sample, amplifying the amplicons described above using the primers described above, amplifying in the same set of reactions the amplicons described above in Universal RNA or another external control—a reference that includes RASGRP1 and APTX RNA species, measuring the $C_t$ values for each reaction, rejecting samples or reactions in which the Ct is above 40 cycles, more preferably rejecting samples or reactions in which the Ct is above 37 cycles, even more preferably rejecting samples or reactions in which the Ct is above 35 cycles and most preferably rejecting samples or reactions in which the Ct is above 30 cycles. Then, the RASGRP1:APTX ratio is calculated as described next.

$$RASGRP1:APTX\ ratio = 2^{-((A-B)-(C-D))}$$

Where
A: Sample RasGRP1 Ct value
B: JY (or Universal) RNA (+) RasGRP1 Ct value
C: Sample APTX Ct Value
D: JY (or Universal) RNA (+) APTX Ct Value Outcome rendered by the assay is compared against the response. To estimate assay performance, Area under the Curve (AUC) value is preferably calculated based on Receiver Operator Characteristic (ROC) curve analysis, for instance, using a MedCalc software package.

In the preferred method, if the ratio exceeds a predetermined threshold, then the patient is classified as being a likely responder. Else, the patient is a non-responder. The predetermined threshold is defined by, preferably, the AUC corresponding to the desired assay performance or another performance criterion such as sensitivity or specificity or a maximized sum of sensitivity and specificity. Thus, the particular threshold value may differ, for instance, due to the reference RNA (Y or Universal or another RNA set) used, but the specification desired performance of the threshold in stratifying patients allows use of different reference RNA and other experimental conditions in an RTPCR assay while generating comparable patient stratification.

This disclosure allows selection of a threshold, wherein the ratio of expression levels RASGRP1 and APTX is compared to the threshold, for identifying a responder to a treatment with a combination of a farnesyl inhibitor and another agent, which is selected from or is a derivative of a member selected from the group consisting of etoposide, teniposide, tamoxifen, sorafenib, paclitaxel, Temozolomide, Topotecan, Trastuzumab and cisplatinum. The selection of the threshold, in a preferred exemplary embodiment, comprises processing a blood sample to generate a ratio of expression levels RASGRP1 and APTX. The threshold is selected to increase one or more of a measure from the set consisting of a positive predictive value of the treatment, a negative predictive value of identifying a responder, an AUC in a ROC analysis, a sensitivity and a specificity. In a preferred embodiment, the expression levels of RASGRP1 or APTX are measured using RT-PCR although other methods of measuring expression of a gene of interest may be substituted.

It should be noted that instead of Universal RNA (from STRATAGENE™ another external control RNA may be used with no loss of generality. However, the predetermined threshold for the RASGRP1:APTX ratio may need to be adjusted. The predetermined threshold may be evaluated using a ROC analysis so as to keep the AUC constant. For instance, using JY RNA (obtained from the JY cell line) as a reference a threshold of 5.2 was determined. Switching to the more widely available standardized Universal RNA resulted in an adjustment of the threshold to 7.3 to ensure that AUC was consistent. The difference in the threshold reflects the different relative presence of RASGRP1 and APTX in the reference RNA. Other reagents may further make a difference in the threshold calculation.

In addition, the threshold may also be adjusted based on the sensitivity or specificity requirements—if any. Thus, when putative non-responders are candidates for an alternative therapy then it is advisable to select a threshold to maximize the number of patients eligible for either therapy to improve the overall likelihood of combating AML in the most patients. In this regard, in view of the ability of younger patients to undergo induction therapy with relatively high remission rates, a different threshold may be used when evaluating such younger patients for treatment with a FTI, alone or in combination with another agent, than the threshold used to evaluate elderly patients who are not offered the induction therapy. Such a threshold may be chosen to reflect a high specificity to identify patients highly likely to respond to treatment with an FTI like tipifarnib. Alternatively, induction therapy in combination with an FTI, even though not known to be synergistic, will provide the patients with timely effective treatment-timeliness being a critical factor in combating AML. This ensures that patients are not denied possible therapy.

Optionally, in an exemplary embodiment, RNA from HMBS is also amplified and detected to check on sample integrity so that an abnormally low value of HMBS RNA flags the sample as being questionable. For HMBS RNA a preferred amplicon is CCTGCCCACTGTGCTTCCTCCTGGCTTCACCATCGGAGCCATCTGCAAGCGGG AAAACCCTCATGAT SEQ ID NO: 7, which is amplified using the primers CCTGCCCACTGTGCTTCCT SEQ ID NO: 8 HMBS upper primer, and ATCATGAGGGTTTTCCCGCT, SEQ ID NO: 9 HMBS, lower primer.

The detection of the amplicons is preferably made using the following probes:
FAM-CATTCAATCTTTTGATGCAGATGGAAACCTG-BHQ 1, RASGPR1, Taqman probe, SEQ ID NO: 10; Gold 540-CACGCCATTCCGAGTATGAGCCATGTAC-BHQ2, APTX, TaqMan probe, SEQ ID NO: 11; and Cy5-GCTTCACCATCGGAGCCATCTGCA-BHQ1, HMBS, TaqMan probe, SEQ ID NO: 12. As will be readily noted, the probes can be varied not only in the choice of the sequences but also as to the specific tags used on them with little loss of generality.

This disclosure also demonstrates that the two-gene ratio RASGRP1:APTX can be rapidly assayed by qPCR performed in a single tube using standardized reagents. This assay has predictive utility in identifying likely responders among newly diagnosed AML as well as relapsed or refractory AML patients—including elderly patients. Further the assay can use a peripheral blood sample instead of the customary bone marrow sample, obtaining which requires a far more invasive a procedure than that required to obtain the peripheral blood sample.

The two-gene ratio is useful in a method for prescribing tipinifarb to a subject diagnosed with a myeloid disorder. In one such method evaluation of the expression of RASGRP1 and APTX is made in a sample, such as bone marrow or blood, by amplification of signals from ribonucleic acid targets using at least one primer from the group consisting of

```
                                            SEQ ID NO: 3
(i)    5'-CGCTTCCGATTGGGCTAC-3'

SEQ ID NO: 4
(ii)   5'-AGAATCAAAATCCTGGCTGATC-3'

SEQ ID NO: 5
(iii)  5'-CTGGACGATCTCATTGACAGC-3'
and

SEQ ID NO: 6
(iv)   5'-CTTGCAACAGTTGGTTACTTCG-3'.
```

Next, the level of expression of genes RASGPR1 is estimated relative to one or more of the group consisting of expression levels of APTX, beta-actin and HMBS, preferably in a single tube in a multiplex format. The ratio of expression levels of RASGRP1 relative to APTX is determined. If the ratio in a subject is greater than a threshold, which preferably is about 5.1 or about 5.2, the subject is prescribed tipifarnib. In a preferred embodiment, tipifarnib is prescribed with another agent synergistic with tipifarnib. Such an agent may be one of or a derivative of a member selected from the group consisting of etoposide, teniposide, tamoxifen, sorafenib, paclitaxel, Temozolomide, Topotecan, Trastuzumab and cisplatinum. The most preferred administration is of tipifarnib and etoposide.

The invention also facilitates a method for administering tipinifarb and etoposide to a patient diagnosed with a myeloid disorder. As before, it is first determined if the ratio of RASGRP1 and APTX expression exceeds a threshold of about 5.1 or about 5.2. And, if the ratio exceeds this threshold, tipifarnib is administered. These and other details are described next with the aid of the following figures, many of which together with parts of the specification are based on, and shared with, the U.S. Pat. No. 7,932,036, which is hereby incorporated by reference.

BRIEF DESCRIPTION OF THE DRAWINGS

FIG. 12B in particular shows the scatter for each patient illustrating the effect of the sample collection protocol. The Y-axis shows the ratio of RASGRP1:APTX in the sample to the RASGRP1:APTX in a calibration/reference RNA, which in this case is JY RNA. Thus, the value on the Y-axis is a ratio of ratios arrived at by the ΔΔCt method. The threshold used in the preferred assay is a threshold based on a desirable stratification of patients using the ΔΔCt method for quantitating the levels of RASGRP1 and APTX.

DETAILED DESCRIPTION

Figure 1:
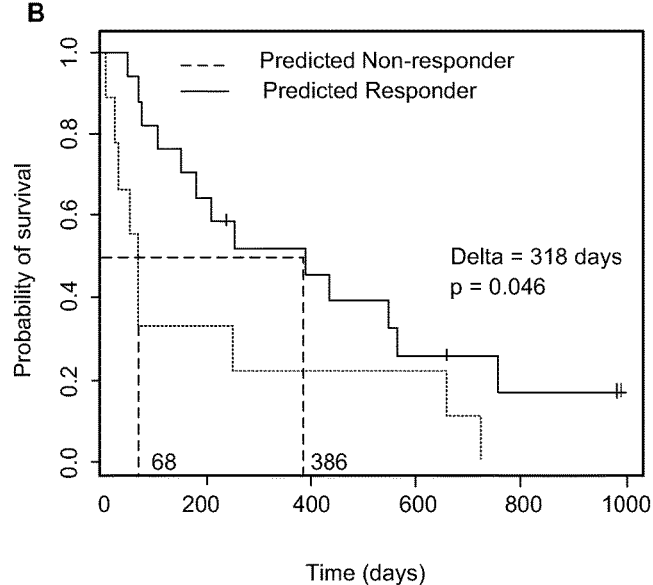
FIG. 1 depicts the performance of the RASGRP1 gene as a predictor of response to tipifarnib in AML. The accuracy rates (A) and Kaplan-Meier survival curves (B) using the RASGRP1 gene classifier in newly diagnosed AML.

The therapeutic agents referred to in this specification include FTIs. They take on a multitude of forms but share the essential inhibitory function of interfering with or lessening the farnesylation of proteins implicated in cancer and proliferative diseases. Preferably, the FTIs are those indicated for the treatment of leukemias such as AML.

Numerous FTIs are within the scope of the disclosure and include those described in U.S. Pat. Nos. 5,976,851; 5,972,984; 5,972,966; 5,968,965; 5,968,952; 6,187,786; 6,169,096; 6,037,350; 6,177,432; 5,965,578; 5,965,539; 5,958,939; 5,939,557; 5,936,097; 5,891,889; 5,889,053; 5,880,140; 5,872,135; 5,869,682; 5,861,529; 5,859,015; 5,856,439; 5,856,326; 5,852,010; 5,843,941; 5,807,852; 5,780,492; 5,773,455; 5,767,274; 5,756,528; 5,750,567; 5,721,236; 5,700,806; 5,661,161; 5,602,098; 5,585,359; 5,578,629; 5,534,537; 5,532,359; 5,523,430; 5,504,212; 5,491,164; 5,420,245; 5,238,922 and US Publication 20030050323. Non-peptidal, so-called "small molecule" therapeutics are preferred. More preferred FTIs are quinolines or quinoline derivatives such as:

7-(3-chlorophenyl)-9-[(4-chlorophenyl)-1H-imidazol-1-yl-methyl]-2,3-dihydro-o-1H,5H-benzo[ij]quinolizin-5-one, 7-(3-chlorophenyl)-9-[(4-chlorophenyl)-1H-imidazol-1-yl-methyl]-1,2-dihydro-o-4H-pyrrolo[3,2,1-ij]quinoline-4-one, 8-[amino(4-chlorophenyl)(1-methyl-1H-imidazol-5-yl), methyl]-6-(3-chlorophenyl)-1,2-dihydro-4H-pyrrolo[3,2,1-ij]quinolin-4-one, and 8-[amino(4-chlorophenyl)(1-methyl-1H-imidazol-5-yl) methyl]-6-(3-chlorophenyl)-2,3-dihydro-1H,5H-benzo [ij]quinolizin-5-one. The most preferred FTI is (B)-6-[amino(4-chlorophenyl)(1-methyl-1H-imidazol-5-yl) methyl]-4-(3-chlorophenyl)-1-methyl-2(1H)-quinolinone).

It is desirable to classify response to treatment to facilitate both and understanding of the effect of the treatment and to compare different treatments. There are many criteria for evaluating treatments. For instance, a count of a thousand neutrophils may suffice to identify a response in some embodiments, while other embodiments may require 1,400 or 1,500 neutrophils. Similarly, the platelet count may vary anywhere from 100,000 to 140,000. And, improvement in one cell line of a certain percentage may be required or in other evaluations improvement in two or even improvement in all three cell lines. The time duration over which such changes are determined may range from one month or two months or even more. In a preferred embodiment, a patient who responds to an FTI is one in whom at least a reduction of more than 50% of blast cells is seen in bone marrow following treatment with the FTI. Typically, the degree of improvement required for partial response tends to be variable, and improvement represented by hematologic improvement is extremely variable between evaluations by different investigators and/or physicians. Alternative similar standards to evaluate a response to the administration of an FTI are intended to be within scope of claims directed to predicting response to treatment—unless a contrary intent is expressly indicated.

In a preferred embodiment, positive responses to treatment comprise rates for Complete Remission (CR), Partial Remission (PR), and Hematologic Improvement (HI). The remaining disease descriptors are Progressive disease (PD) with the remainder of the non-responders adjudged to be exhibiting Stable disease (SD). Each of the positive responder classifications are described next.

Complete remission (CR) may be marked by bone marrow showing less than 5% myeloblasts with normal maturation of all cell lines, an ANC of at least 1000/µL and a platelet count of 100,000 µL, absence of blasts in peripheral blood, absence of identifiable leukemic cells in the bone marrow, clearance of disease-associated cytogenetic abnormalities, and clearance of any previously existing extramedullary disease. A CR must be confirmed 4 to 6 weeks after the initial documentation. If possible, at least one bone marrow biopsy should be performed to confirm the CR. With CR it is expected bone marrow will appear to be normal with fewer than five percent blasts, normal maturation, and no dysplasia. In the peripheral blood, a haemoglobin of greater than 11 grams, neutrophils of over 1,500 per millimeter squared and platelets over 100,000, no blasts, and no dysplasia will be encountered. Further, to consider AML cured, ideally the risk of relapse in a patient with CR must be the same as the risk of AML in the general population.

Partial remission (PR) is preferably identified by the presence of trilineage hematopoiesis in the bone marrow with recovery of ANC and platelets to the above stated levels, but with 5 to 25% bone marrow blasts, and at least 50% decrease in bone marrow blast percentage from baseline. A PR must be confirmed 4 to 6 weeks after the initial documentation.

Hematologic Improvement (HI) is preferably marked by at least 50% decrease in marrow blasts or decrease in any measurable extramedullary disease, recovery of ANC to 500 to 1000 µL, platelet count to 20,000 to 100,000 µL, or improvement in transfusion requirements.

Stable disease (SD) is identified by any response to treatment not meeting CR, PR, HI, or PD criteria.

Progressive disease (PD) is marked by any one of the following:
>50% increase in bone marrow blast percentage from best assessment
>50% increase in circulating blasts
New appearance of circulating blasts (on at least 2 consecutive occasions)
Development of extramedullary disease
In patients who present with an initial marrow blast percentage sufficiently high to preclude the ability to base disease progression on a >50% increase in marrow blast percentage, disease progression should be based upon peripheral blood criteria, new appearance of circulating blasts (on at least 2 consecutive occasions), and/or development of extramedullary disease.

The duration of response is preferably measured from the time measurement criteria are met for CR or PR (whichever is first recorded) until the first date that recurrent or progressive disease is objectively documented. The duration of CR is measured from the time measurement criteria are first met for CR until the first date that recurrent disease is objectively documented.

The duration of stable disease is measured in patients with stable disease from the start of the treatment until the criteria for progression are met.

Progression-Free Survival ("PFS") represents the time between study entry and the first date of objective documentation of recurrent or progressive disease, or the occurrence of death from any cause. Overall Survival is measured from time of enrollment onto this study to time of death.

The mere presence of nucleic acid sequences having the potential to express proteins or peptides ("genes") within the genome is not determinative of whether a protein or peptide is expressed in a given cell. Whether or not a given gene capable of expressing proteins or peptides does so and to what extent such expression occurs, if at all, is determined by a variety of complex factors. Irrespective of difficulties in understanding and assessing these factors, assaying gene expression can provide useful information about the cellular response to a given stimulus such as the introduction of a drug or other therapeutic agent. Relative indications of the degree to which genes are active or inactive can be found in gene expression profiles. The gene expression profiles are used to identify and treat patients who will likely benefit from a given therapy or exclude patients from a given therapy where the patient likely would experience little or no beneficial response to the drug or therapy.

Preferred methods for establishing gene expression profiles (including those used to arrive at the relevant biological pathways) include determining the amount of RNA that is produced that can code for a protein or peptide. This is accomplished by reverse transcription PCR (RT-PCR), competitive RT-PCR, real time RT-PCR, differential display RT-PCR, Northern Blot analysis and other related tests. While it is possible to conduct these techniques using individual PCR reactions, it is best to amplify copy DNA (cDNA) or copy RNA (cRNA) produced from mRNA. Some methods for determining gene expression can be found in U.S. Pat. Nos. 6,271,002; 6,218,122; 6,218,114; and 6,004,755.

Figure 6:
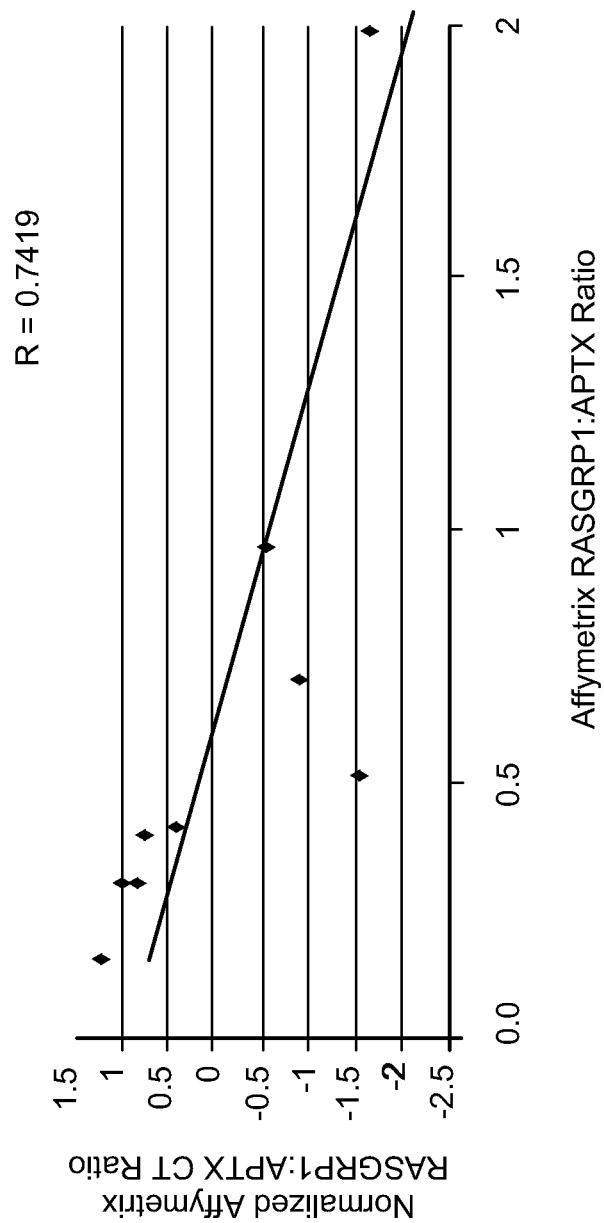
FIG. 6 depicts the correlation of Affymetrix and qPCR data. Nine RNA samples that were analyzed on both the Affymetrix GeneChip and by qPCR were compared by linear regression analysis. The Y-axis is used to plot the qPCR values in the form of a normalized ΔCt corresponding to a ratio of RASGRP1:APTX. It should be noted that this value, strictly speaking, is not a ratio but a normalized Δ-Ct corresponding to the ratio even though the terms are used interchangeably. As a result, as the level of RASGRP1 increases, its corresponding Ct value decreases and all else being the same, the ΔCt value decreases. The X-axis represents the corresponding RASGRP1:APTX ratio values generated from the array data for the same samples, which values increase as the ratio increases. As a result the slope of the line showing the correlation between the normalized Δ-Ct and the array generated RASGRP1:APTX ratios is negative.
Figure 7:
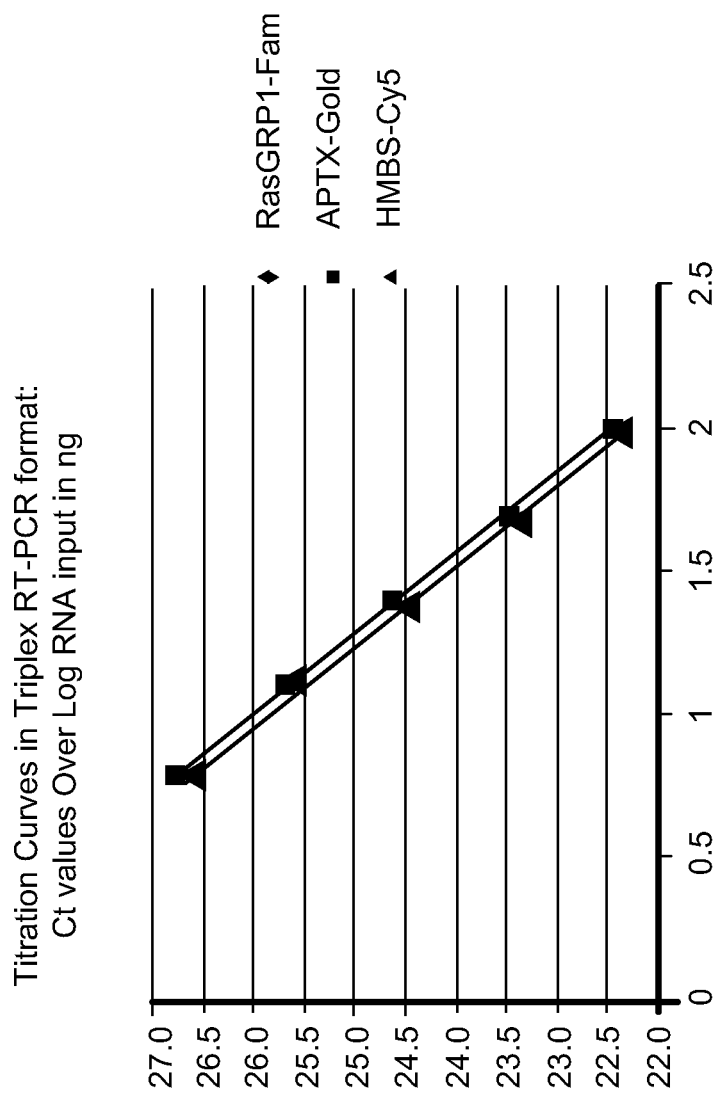
FIG. 7 depicts the amplification of RasGRP1, APTX and HMBS RNA in a triplex format in a single tube showing the required close correspondence, low variability and high reproducibility.

One preferred method involves computing the two-gene ratio RASGRP1:APTX to determine whether a person is likely to respond to the use of an FTI therapeutic agent. The term 'ratio' or the 'two-gene ratio RASGRP1:APTX' as applied to gene expression values has a range of technical interpretations in this disclosure that are readily discerned from the context. At a basic level the meaning is the same although the form may differ. For instance, when using qPCR techniques, a $\Delta C_t$ value corresponding to a ratio of two genes of interest is readily generated, as is well known to one having ordinary skill in the art. This value may be generated by using normalized $C_t$ values for the expression levels of each of the genes by for instance, subtracting the mean $C_t$ value for that gene and dividing by the standard deviation in the $C_t$ values for that gene. The difference between such normalized $C_t$ values for the two genes, the $\Delta C_t$ value, corresponds to the ratio of expression of the genes in that as the ratio increases, the $\Delta C_t$ value decreases and vice-versa. Examples of such normalized $\Delta C_t$ values are seen on the Y-axis of FIG. 6 for RASGRP1 and APTX. Such $\Delta C_t$ values, or even normalized $\Delta C_t$ values may be referred to as the two-gene ratio RASGRP1:APTX in this disclosure. An example is in FIG. 3A which shows a threshold of 0 in terms of $\Delta C_t$ value on the Y-axis such that responders are below the threshold. This threshold of 0 corresponds to a threshold of 1 when two-gene ratio RASGRP1:APTX is expressed in terms of array data, such as those plotted along the X-axis of FIG. 6. FIG. 6 merely illustrates that it is readily possible to go from one way of determining the RASGRP1:APTX ratio to another. Alternatively, the ratio may be expressed as a positive number based on the $\Delta\Delta C_t$ value, which compares various samples to a standard calibrator/reference RNA. Use of such a common calibrator makes an assay more portable and reliable since the threshold can and does change based on the experimental conditions since the threshold is primarily defined by its performance in stratifying patients in a test environment. In a preferred embodiment using RTPCR, the two-gene ratio RASGRP1:APTX, expressed as a positive number based on the $\Delta\Delta C_t$ value as described elsewhere in this disclosure, leads to a value of 5.2 for stratifying responders to tipifarnib from non-responders to tipifarnib. Example two-gene ratio values of RASGRP1:APTX, expressed as a positive number based on the $\Delta\Delta C_t$ values, are plotted on the Y-axis of FIG. 12B and are also referred to as two-gene ratio RASGRP1:APTX with the context making clear which interpretation should be used. Strictly speaking, a person having ordinary skill in the art will realize that a threshold or two-gene ratio RASGRP1:APTX, expressed as a value based on one or more of the $\Delta\Delta C_t$ value, in terms of array data, as a $\Delta C_t$ value and just the $\Delta\Delta C_t$ value while comparable may not lend themselves to ready interconvertability in the absence of additional information to aid in such a mapping. The claims and description herein should be read in light of this consideration. The two-gene ratio RASGRP1:APTX is indicated, for clarity, as the two-gene $\Delta\Delta C_t$ ratio RASGRP1:APTX or the two-gene $\Delta C_t$ ratio RASGRP1:APTX or the $\Delta\Delta C_t$ threshold or the $\Delta C_t$ threshold, but when such clarification is not provided the context readily provides the correct interpretation.

Having established a threshold to distinguish a responder from a non-responder, the two-gene ratio is fixed in a medium such as a computer readable medium as described below. A patient sample is obtained that contains diseased cells (such as hematopoietic blast cells in the case of AML). In a preferred embodiment, sample RNA is then obtained and amplified from the diseased patient cell and amplified using PCR and the two-gene ratio calculated with the aid of an external normalization control. Then, in a preferred embodiment, if the two-gene ratio is greater than a predetermined threshold, the patient is identified as a likely responder, else as a non-responder.

In similar fashion, the two-gene ratio can be used to monitor response to a treatment comprising an FTI at various periods throughout the course of treatment. If the two-gene ratio is consistent with a responder then the patient's therapy is continued. If it is not, then the patient's therapy is altered. Such analysis permits intervention and therapy adjustment prior to detectable clinical indicia or in the face of otherwise ambiguous clinical indicia.

Preferred embodiments may cover representations of the gene expression profiles useful for treating, diagnosing, prognosticating, staging, and otherwise assessing diseases that are reduced to a medium that can be automatically read such as computer readable media (magnetic, optical, and the like). Preferred embodiments can also include instructions for assessing the gene expression profiles in such media. For example, preferred embodiments may comprise a CD ROM having computer instructions for comparing gene expression profiles of the portfolios of genes described above. The preferred embodiments may also have gene expression profiles digitally recorded therein so that they may be compared with gene expression data from patient samples. Alternatively, the profiles can be recorded in different representational format. A graphical recordation is one such format. Clustering algorithms such as those incorporated in "OMNIVIZ" and "TREE VIEW" computer programs mentioned above can best assist in the visualization of such data.

The biological effect of a drug may be a consequence of drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In addition to the preferred FTI's, the preferred drugs include those that modulate the MAPK/ERK signaling pathways, TGF-β, WNT or apoptotic pathways. These include, without limitation, tyrosine kinase inhibitors, MEK kinase inhibitors, P13K kinase inhibitors, MAP kinase inhibitors, apoptosis modulators and combinations thereof. Exemplary drugs that are most preferred among these are the "GLEEVEC" tyrosine kinase inhibitor of Novartis, U-0126 MAP kinase inhibitor, PD-098059 MAP kinase inhibitor, SB-203580 MAP kinase inhibitor, and antisense, ribozyme, and DNAzyme Bcl-XL anti-apoptotics. Examples of other useful drugs include, without limitation, the calanolides of U.S. Pat. No. 6,306,897; the substituted bicyclics of U.S. Pat. No. 6,284,764; the indolines of U.S. Pat. No. 6,133,305; and the antisense oligonucleotides of U.S. Pat. No. 6,271,210.

Pharmaceutically useful compositions comprising the drugs described herein may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the drug. The effective amount of the drug may vary according to a variety of factors such as the individual's condition, weight, sex and age. Other factors include the mode of administration. The pharmaceutical compositions may be provided to the individual by a variety of routes such as subcutaneous, topical, oral and intramuscular.

The drugs described herein include chemical derivatives of the base molecules of the drug. That is, they may contain additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition or activity while minimizing any potential toxicity. In addition, co-administration or sequential administration of other agents may be desirable.

The drugs described herein can be administered in a wide variety of therapeutic dosage forms in conventional vehicles for administration. For example, the drugs can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a modulating agent.

For combination treatment with more than one active agent, where the active agents are in separate dosage formulations, the active agents can be administered concurrently, or they each can be administered at separately staggered times.

The dosage regimen utilizing the compounds or modulators described herein is selected in accordance with a variety of factors including type, species, age, weight, sex and medical condition of the patient; the severity of the condition to be treated; the route of administration; the renal and hepatic function of the patient; and the particular drug employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The drugs described herein form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

The compounds or modulators may alternatively be administered parenterally via injection of a formulation consisting of the active ingredient dissolved in an inert liquid carrier. Injection may be either intramuscular, intraluminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

All citations herein are hereby incorporated herein by reference. Further, also incorporated by reference is the previously filed U.S. patent applications 60/340,938 filed Oct. 30, 2001; 60/338,997 filed Oct. 30, 2001, 60/340,081 filed Oct. 30, 2001, 60/341,012 filed Oct. 30, 2001, 10/283,975 filed on Oct. 30, 2002 and 11/589,660 filed on Oct. 30, 2006, including all references cited therein. The disclosure is further illustrated by the following non-limiting examples.

Example 1

Materials and Methods
Clinical Evaluation

In an exemplary example, bone marrow samples are collected from an open label, multicenter, non-comparative phase 2 study investigating the efficacy and safety of farnesyltransferase inhibition with tipifarnib (R115777, ZARNESTRA®) in older adults with previously untreated, poor-risk AML.

Sample Collection and Processing

Bone marrow samples were collected from consenting patients before treatment with tipifarnib followed by mononuclear cells preferably being processed on site. Bone marrow aspirates were diluted with PBS and centrifuged with ficoll-diatrizoate (1.077 g/ml). Enriched leukemic blood cells were washed twice with PBS, resuspended in FBS with 10% DMSO and immediately frozen at −70° C. to −80° C. Total RNA was extracted from cell samples using the Trizol Kit (Qiagen, Santa Clarita, Calif.). RNA quality may be determined by assessing the presence of ribosomal bands on an Agilent Bioanalyzer. Good quality samples were further processed for microarray analysis. DNA was isolated from the same sample of Trizol-processed bone marrow as per the manufacturer's instructions (Qiagen, Santa Clarita, Calif.). Samples were assayed for global gene expression, N-RAS mutations, and/or qPCR of specific genes (FIG. 1).

N-RAS Mutational Status

Analysis of activating mutations in N-RAS was determined by PCR and RFLP analysis as previously described. End et al. (2001). Exons 1 and 2 of the N-RAS gene were simultaneously amplified in a single multiplex reaction and an aliquot was used for a second round of PCR. Resistance to cleavage at natural or primer induced restriction enzyme sites in second-round amplicons indicated the presence of a mutation that had abolished the site at the loci being analyzed. Restriction enzymes for the analysis of specific loci were Bsl I (N-ras codons 12 and 13), Msc I (N-ras codon 61, positions 1 and 2), and Bfa I (N-ras codon 61, position 3). Reactions were digested overnight and PCR products were analyzed on an Agilent Bioanalyzer.

Microarray Analysis

Synthesis of cDNA and cRNA were performed according to Affymetrix (Santa Clara, Calif.) protocols. Since the yield of many samples was low, two rounds of linear amplification were performed as previously described in US Patent Publication No. 20070048782. For hybridization, 11 µg of cRNA were fragmented randomly by incubation at 94° C. for 35 min in 40 mM Tris-acetate, pH 8.1, 100 mM potassium acetate, and 30 mM magnesium acetate. Fragmented cRNA was hybridized to U133A arrays at 45° C. for 16 h in a rotisserie oven set at 60 rpm. Following hybridization, arrays were washed (with 6×SSPE and 0.5×SSPE containing Triton X-100 (0.005%)), and stained with streptavidin-phycoerythrin (SAPE; Molecular Probes, Eugene, Oreg.).

Quantification of bound labeled probe was conducted using the Agilent G2500A GeneArray scanner (Agilent Technologies, Palo Alto, Calif.).

The total fluorescence intensity for each array was scaled to the uniform value of 600. Chip performance was quantified by calculating a signal to noise ratio (raw average signal/noise). Chips were removed from further analysis if their signal-to-noise ratio was less than 20 or if the present calls on the chip was less than 30%. Genes were only included in further analysis if they were called "present" in at least 10% of the chips. Approximately 12,000 Affymetrix probe sets remained following this cut-off. The quality of the gene expression data were further controlled by identifying outliers based on principal components analysis and by analyzing the normal distributions of the gene intensities (Partek Pro V5.1). The microarray data have been deposited in NCBIs Gene Expression Omnibus (GEO, http://www.ncbi.nlm.nih.gov/geo/).

Response Definitions

Response to tipifarnib was defined as patients who had a complete response (CR), a partial response (PR), or hematological improvement (HI). Briefly, HI was defined as any bone marrow blast count less than 5% or a reduction in bone marrow blasts by at least half Progressive disease (PD) was defined as either >50% increase in bone marrow or circulating blast % from baseline, or new appearance of circulating blasts (on at least 2 consecutive occasions). Stable disease (SD) was defined as any response not meeting CR, PR, HI, or PD criteria.

Statistical Analysis

Receiver Operator Characteristic (ROC) analysis was utilized to test the overall predictive value of individual genes and/or multigene classifiers. The following gene filtering criteria were used to identify genes differentially expressed between responders and patients with progressive disease: Specificity for identifying "responder" with 100% sensitivity>=40%, T-test p value (log 2 transformed data with unequal variance)<0.05, fold change>2. The genes that passed these criteria were ranked by AUC (Area under the ROC curve).

To build a classifier the response score was used to calculate each patient's likelihood of responding to tipifarnib therapy. The score was defined as the linear combination of weighted expression signals with the t-statistic as the weight. The threshold was determined from the ROC curve of the training set to ensure 100% sensitivity and the highest specificity. To determine how many genes needed to be included in the predictor, leave-one-out cross validation (LOOCV) was carried out. The response scores for the 'left-out' samples based on different numbers of genes were recorded. The performances of the predictors with different numbers of genes were assessed based on misclassification error rate, sensitivity, specificity, p values measuring the separation of Kaplan-Meier curves of the two predicted groups. And the best predictor was selected accordingly.

The Top Scoring Pair (TSP) algorithm was first introduced by Geman et al. (2004). In essence, the algorithm ranks all the gene pairs (genes i and j) based on the absolute difference (Dij) in the frequency of event where gene i has higher expression value than gene j in samples among class C1 to C2. In the cases of there are multiple top scoring pairs (all sharing the same Dij), the top pair by a secondary rank score that measures the magnitude to which inversions of gene expression levels occur from one class to the other within a pair of genes is selected. The top pair with highest frequency of absolute Dij>2 fold in all samples will be selected as candidate pair. The candidate pair was then assessed in an independent testing data set.

Leave-one-out cross validation (LOOCV) was carried out in the training data set to evaluate how the algorithm perform. The performances of the predictors were assessed based on maximum misclassification error rate. All the statistical analyses were done using R(R Development Core Team, 2006).

Real-Time Quantitative RT-PCR

For each sample, 1 µg of total RNA (as assessed by $OD_{260}$) was reversed transcribed using the High Capacity cDNA Reverse Transcription kit (Applied Biosystems, Foster City, Calif.) according to the manufacturer's instructions. Samples were then incubated at 25° C. for 10 minutes and then 37° C. for 30 minutes for optimum RNA conversion. QPCR was performed using the ABI Prism 7900HT sequence detection system (Applied Biosystems, Foster City, Calif.) with all samples run in triplicate. Each reaction contained 5 µl TaqMan® Universal PCR Master Mix containing UNG (Applied Biosystems, Foster City, Calif.), 4.5 µl of cDNA template and 0.5 µl of 20× Assay on Demand Gene Expression Assay Mix or 9 pmol of both forward and reverse primer and 2.5 pmol of probe (Applied Biosystems, Foster City, Calif.), in a total reaction volume of 10 µl. All primer, probe sets were chosen due to the small amplicon size (less than 100 nucleotides) and FAM fluorogenic probes were used. Primers and probes used were APTX (product number 4331182 Applied Biosystems) and RASGRP1 (product number 4351372 Applied Biosystems). The RASGRP1:APTX expression ratio was calculated by normalizing the raw Ct values by subtracting the mean Ct from the sample set, dividing by the standard deviation, and then calculating the difference of the normalized Ct values of each gene (APTX−RASGRP1).

Results

This study examined gene expression profiles of leukemic bone marrow samples from patients enrolled in a Phase 2 clinical trial of the farnesyltransferase inhibitor tipifarnib in elderly patients with previously untreated poor-risk acute myelogenous leukemia. Lancet et al. (2006). Bone marrow from 67 patients was collected before treatment with tipifarnib and leukemic myeloid cells were enriched by Ficoll-density centrifugation (Table 1). Good quality total RNA from 13 responders (9 CR, 4 HI), 8 stable disease and 13 progressive disease patients was amplified, labeled, and hybridized to the Affymetrix U133A GeneChip. A total of 30 samples were evaluated by qPCR for validation of specific genes and 32 samples were evaluated for N-RAS mutational status.

TABLE 1

Comparison of profiled patients.

| Parameter | All treated patients | PGx profiled patients |
|---|---|---|
| Total patients, n | 158 | 67 |
| microarray assay, n | | 34 |
| qPCR assay, n | | 30 |
| N-Ras assay, n | | 32 |
| N-Ras mutation, n (%) | | 11 (34) |
| median age, y (range) | 74 (34-85) | 73 (63-85) |
| sex, n male (%) | 95 (60) | 41 (61) |
| Prior MDS, yes (%) | 119 (75) | 48 (72) |
| CR, no. (%) | 22 (14) | 14 (21) |
| PR, no. (%) | 3 (2) | 1 (2) |
| HI, no. (%) | 12 (8) | 7 (10) |
| SD, no. (%) | 50 (32) | 15 (22) |
| PD, no. (%) | 58 (37) | 30 (44) |
| NE, no. (%) | 13 (8) | 0 (0) |

CR = complete response; PR = partial response; HI = hematological improvement, SD = stable disease, PD = progressive disease, NE = not evaluable; PGx = pharmacogenomics Ras mutational status and patient outcome.

DNA from the bone marrow of 32 AML patients was screened for N-Ras activating mutations (codons 12, 13, 61). Thirty-four percent (11/32) of patients exhibited N-Ras mutations with one patient having mutations at multiple codons (Table 2). There was no statistically significant correlation between N-RAS mutational status and response to tipifarnib or overall survival.

TABLE 2

| SUBJID | RESPONSE | N-Ras Mutation | OS | Alive | Microarray | qPCR | SEX | AGE | Prior MDS |
|---|---|---|---|---|---|---|---|---|---|
| 100101 | HI | ND | 378 | NO | ND | YES | MALE | 68 | NO |
| 100104 | PD | ND | 728 | NO | YES | YES | FEMALE | 63 | NO |
| 100109 | PD | ND | 68 | NO | YES | YES | FEMALE | 81 | NO |
| 100110 | CR | ND | 983 | YES | YES | YES | FEMALE | 74 | NO |
| 100112 | PD | ND | 169 | NO | ND | YES | FEMALE | 69 | YES |
| 100113 | CR | ND | 211 | NO | ND | YES | MALE | 82 | YES |
| 100116 | PD | ND | 14 | NO | ND | YES | FEMALE | 72 | YES |
| 100121 | SD | ND | 252 | NO | YES | ND | MALE | 72 | YES |
| 100204 | SD | N-12 | 493 | NO | ND | ND | FEMALE | 69 | YES |
| 100205 | PD | WT | 754 | NO | YES | ND | MALE | 74 | YES |
| 100208 | PD | WT | 29 | NO | ND | ND | MALE | 76 | YES |
| 100209 | PD | N61(1, 2) | 209 | NO | YES | ND | MALE | 73 | YES |
| 100210 | PD | N-12, N-13 | 654 | NO | YES | ND | MALE | 68 | YES |
| 100212 | SD | N-12 | 1200 | YES | ND | ND | MALE | 70 | YES |
| 100213 | CR | WT | 257 | NO | YES | ND | FEMALE | 81 | YES |
| 100214 | CR | N-13 | 395 | NO | ND | ND | FEMALE | 73 | YES |
| 100215 | SD | WT | 54 | NO | ND | ND | MALE | 82 | NO |
| 100216 | SD | N-13 | 116 | NO | ND | ND | MALE | 77 | YES |
| 100302 | PD | N-12 | 48 | NO | YES | ND | FEMALE | 73 | NO |
| 100307 | HI | WT | 179 | NO | YES | ND | MALE | 68 | YES |
| 100310 | SD | WT | 242 | NO | ND | ND | FEMALE | 76 | YES |
| 100316 | SD | WT | 273 | NO | ND | ND | FEMALE | 66 | NO |
| 100317 | PD | WT | 39 | NO | ND | ND | MALE | 76 | NO |
| 100319 | SD | WT | 233 | NO | YES | ND | MALE | 71 | NO |
| 100320 | HI | WT | 374 | NO | ND | ND | FEMALE | 78 | NO |
| 100322 | CR | WT | 237 | YES | YES | ND | MALE | 73 | YES |
| 100324 | HI | WT | 248 | NO | YES | ND | MALE | 85 | YES |
| 100330 | HI | N-12 | 153 | NO | YES | ND | FEMALE | 67 | NO |
| 100333 | SD | N-12 | 364 | NO | YES | ND | MALE | 65 | YES |
| 100336 | CR | N-12 | 67 | NO | YES | ND | MALE | 80 | YES |
| 100337 | PD | WT | 38 | NO | ND | ND | MALE | 72 | YES |
| 100338 | PD | N-12 | 8 | NO | YES | ND | MALE | 78 | NO |
| 100339 | PD | WT | 25 | NO | YES | ND | MALE | 75 | NO |
| 100340 | SD | WT | 32 | NO | ND | ND | FEMALE | 83 | NO |
| 100341 | CR | WT | 433 | NO | YES | ND | MALE | 67 | YES |
| 100604 | SD | WT | 64 | NO | YES | ND | MALE | 63 | YES |
| 100605 | PD | WT | 74 | NO | ND | ND | MALE | 67 | YES |
| 101008 | CR | WT | 548 | NO | YES | ND | MALE | 82 | NO |
| 101021 | CR | ND | 991 | YES | YES | YES | FEMALE | 69 | YES |
| 101025 | CR | ND | 735 | YES | ND | YES | MALE | 70 | YES |
| 101029 | PD | ND | 64 | NO | ND | YES | MALE | 70 | YES |
| 101038 | SD | ND | 151 | NO | YES | YES | FEMALE | 75 | YES |
| 101039 | PD | ND | 50 | NO | ND | YES | FEMALE | 85 | YES |
| 101043 | SD | ND | 200 | NO | YES | ND | FEMALE | 79 | YES |
| 101046 | PD | ND | 53 | NO | YES | YES | FEMALE | 66 | YES |
| 101049 | CR | WT | 564 | NO | YES | ND | MALE | 65 | YES |
| 101057 | CR | WT | 386 | NO | YES | ND | MALE | 85 | YES |
| 101067 | PD | ND | 88 | NO | ND | YES | FEMALE | 76 | YES |
| 101069 | PD | ND | 94 | NO | ND | YES | MALE | 81 | YES |
| 101075 | HI | ND | 659 | YES | YES | YES | MALE | 71 | YES |
| 101077 | SD | ND | 574 | YES | YES | ND | FEMALE | 75 | YES |
| 101078 | PD | ND | 190 | NO | ND | YES | FEMALE | 77 | NO |
| 101079 | PD | ND | 429 | NO | ND | YES | FEMALE | 70 | YES |
| 101083 | PD | ND | 71 | NO | ND | YES | MALE | 73 | YES |
| 101091 | CR | ND | 671 | YES | ND | YES | MALE | 71 | YES |
| 101092 | PD | ND | 136 | NO | ND | YES | FEMALE | 69 | YES |
| 101094 | HI | ND | 579 | YES | ND | YES | MALE | 65 | YES |
| 101095 | PD | ND | 108 | NO | YES | YES | MALE | 82 | YES |
| 101096 | CR | ND | 390 | YES | ND | YES | MALE | 69 | YES |
| 101101 | PD | ND | 91 | NO | ND | YES | MALE | 69 | YES |
| 101102 | PD | ND | 76 | NO | YES | YES | MALE | 69 | YES |
| 101103 | PD | ND | 29 | NO | ND | YES | FEMALE | 80 | NO |
| 101108 | PR | ND | 123 | NO | NO | YES | MALE | 70 | YES |
| 101109 | SD | ND | 656 | YES | YES | ND | MALE | 68 | YES |
| 101114 | PD | ND | 69 | NO | YES | YES | MALE | 72 | YES |
| 101121 | PD | ND | 43 | NO | ND | YES | MALE | 78 | NO |
| 101122 | PD | ND | 44 | NO | ND | YES | FEMALE | 80 | NO |

ND = not determined;
WT = wildtype;
CR = complete response;
PR = partial response;
HI = hematological improvement,
SD = stable disease,
PD = progressive disease,
OS = Overall survival.

Identification of Predictive Genes from the Newly Diagnosed AML Cohort

The next aim was to identify genes predictive of response to tipifarnib in the newly diagnosed AML population. To this end discovery experiments were performed in the 13 responders (9 CR and 4 HI) and 13 patients with progressive disease. Patients with stable disease were not utilized in this analysis since these patients cannot be clearly defined as either responders or non-responders. Using the same approach as was utilized for identifying markers for relapsed and refractory AML (20070048782) we identified 45 probesets (corresponding to 38 unique genes) that were predictive of response (Table 3). The selection criteria aimed at identifying genes that would predict responders with a high sensitivity (approaching 100%) with a specificity cut-off of 40% and a mean gene expression difference of at least two-fold. The genes were ranked based on the area under the curve (AUC) defined from a receiver operator characteristic (ROC) analysis of the training set. This value represents the overall predictive value of the gene with an AUC of 1.0 indicating perfect classification. Each gene was first tested on the training set using a LOOCV method. The top gene, the RAS guanyl-releasing protein 1 (RASGRP1), showed an AUC of 0.95.

TABLE 3

45 probesets predictive of response to tipifarnib in newly diagnosed AML

| Probe Set ID | Gene Symbol | Gene Title | pvalue | spec | tstat | FC | AUC |
|---|---|---|---|---|---|---|---|
| 205590_at | RASGRP1 | RAS guanyl releasing protein 1 | 2.64E−06 | 0.54 | 6.40 | 4.01 | 0.95 |
| 217028_at | CXCR4 | chemokine (C—X—C motif) receptor 4 | 4.41E−05 | 0.69 | 5.08 | 2.35 | 0.92 |
| 206687_s_at | PTPN6 | protein tyrosine phosphatase, non-receptor type 6 | 8.23E−05 | 0.77 | −4.75 | −2.15 | 0.91 |
| 210439_at | ICOS | inducible T-cell co-stimulator | 1.27E−04 | 0.77 | 4.56 | 3.81 | 0.91 |
| 206641_at | TNFRSF17 | tumor necrosis factor receptor superfamily, member 17 | 3.79E−02 | 0.62 | 2.24 | 2.55 | 0.91 |
| 213539_at | CD3D | CD3d molecule, delta (CD3-TCR complex) | 1.75E−04 | 0.69 | 4.63 | 2.82 | 0.91 |
| 208018_s_at | HCK | hemopoietic cell kinase | 2.62E−04 | 0.62 | −4.28 | −3.14 | 0.90 |
| 203063_at | PPM1F | protein phosphatase 1F (PP2C domain containing) | 3.66E−04 | 0.85 | −4.17 | −2.31 | 0.90 |
| 208130_s_at | TBXAS1 | thromboxane A synthase 1 | 2.70E−04 | 0.46 | −4.26 | −2.51 | 0.89 |
| 216834_at | RGS1 | regulator of G-protein signalling 1 | 3.90E−04 | 0.62 | 4.16 | 3.48 | 0.87 |
| 213388_at | PDE4DIP | phosphodiesterase 4D interacting protein (myomegalin) | 1.47E−03 | 0.54 | −3.64 | −2.01 | 0.86 |
| 38487_at | STAB1 | stabilin 1 | 7.95E−04 | 0.54 | −3.87 | −2.45 | 0.86 |
| 210982_s_at | HLA-DRA | major histocompatibility complex, class II, DR alpha | 4.23E−03 | 0.69 | −3.25 | −3.07 | 0.85 |
| 210321_at | GZMH | granzyme H (cathepsin G-like 2, protein h-CCPX) | 1.64E−03 | 0.54 | 3.55 | 2.83 | 0.85 |
| 217147_s_at | TRAT1 | T cell receptor associated transmembrane adaptor 1 | 1.19E−03 | 0.54 | 3.72 | 2.82 | 0.85 |
| 206298_at | ARHGAP22 | Rho GTPase activating protein 22 | 7.89E−04 | 0.62 | −3.88 | −2.19 | 0.85 |
| 202990_at | PYGL | phosphorylase, glycogen; liver | 1.95E−03 | 0.46 | −3.50 | −2.01 | 0.85 |
| 221671_x_at | IGKC | immunoglobulin kappa constant | 1.62E−03 | 0.46 | 3.56 | 3.10 | 0.85 |
| 221651_x_at | IGKC | immunoglobulin kappa constant | 1.65E−03 | 0.46 | 3.57 | 2.92 | 0.85 |
| 207651_at | GPR171 | G protein-coupled receptor 171 | 1.13E−03 | 0.62 | 3.70 | 3.01 | 0.85 |
| 202988_s_at | RGS1 | regulator of G-protein signalling 1 | 1.48E−03 | 0.54 | 3.59 | 2.95 | 0.84 |
| 213418_at | HSPA6 | heat shock 70 kDa protein 6 | 1.63E−02 | 0.62 | −2.61 | −2.34 | 0.83 |
| 209901_x_at | AIF1 | allograft inflammatory factor 1 | 3.52E−03 | 0.54 | −3.24 | −2.48 | 0.83 |
| 205488_at | GZMA | granzyme A | 4.43E−03 | 0.46 | 3.18 | 2.75 | 0.83 |
| 217022_s_at | IGHA1 | immunoglobulin heavy constant alpha 1 | 3.43E−03 | 0.69 | 3.36 | 2.56 | 0.83 |
| 207339_s_at | LTB | lymphotoxin beta (TNF superfamily, member 3) | 1.34E−03 | 0.46 | 3.65 | 2.40 | 0.83 |
| 206337_at | CCR7 | chemokine (C-C motif) receptor 7 | 1.14E−03 | 0.54 | 3.71 | 2.08 | 0.83 |
| 208894_at | HLA-DRA | major histocompatibility complex, class II, DR alpha | 6.14E−03 | 0.46 | −3.05 | −2.58 | 0.82 |
| 39729_at | PRDX2 | peroxiredoxin 2 | 5.81E−03 | 0.54 | 3.05 | 2.13 | 0.82 |
| 209500_x_at | TNFSF13 | tumor necrosis factor (ligand) superfamily, member 13 | 1.23E−03 | 0.46 | −3.68 | −2.02 | 0.82 |
| 214677_x_at | IGL@ | immunoglobulin lambda locus | 4.69E−03 | 0.46 | 3.17 | 2.86 | 0.82 |
| 210314_x_at | TNFSF13 | tumor necrosis factor (ligand) superfamily, member 13 | 3.48E−03 | 0.46 | −3.24 | −2.05 | 0.81 |
| 209138_x_at | IGL@ | Immunoglobulin lambda locus | 4.17E−03 | 0.54 | 3.17 | 3.41 | 0.80 |
| 207831_x_at | DHPS | deoxyhypusine synthase | 1.09E−02 | 0.62 | −2.77 | −2.05 | 0.80 |
| 215121_x_at | IGL@ | immunoglobulin lambda locus | 1.20E−02 | 0.46 | 2.72 | 4.42 | 0.79 |
| 215946_x_at | CTA-246H3.1 | similar to omega protein | 1.10E−02 | 0.46 | 2.76 | 2.46 | 0.79 |
| 204069_at | MEIS1 | Meis1, myeloid ecotropic viral integration site 1 homolog | 1.01E−02 | 0.62 | −2.89 | −2.14 | 0.78 |
| 204698_at | ISG20 | interferon stimulated exonuclease gene 20 kDa | 6.93E−03 | 0.46 | 2.95 | 2.39 | 0.78 |
| 209906_at | C3AR1 | complement component 3a receptor 1 | 1.49E−02 | 0.54 | −2.65 | −2.05 | 0.77 |
| 205608_s_at | ANGPT1 | angiopoietin 1 | 6.40E−03 | 0.46 | −3.11 | −2.18 | 0.76 |
| 205927_s_at | CTSE | cathepsin E | 2.02E−02 | 0.46 | 2.55 | 2.05 | 0.76 |
| 215051_x_at | AIF1 | allograft inflammatory factor 1 | 1.54E−02 | 0.62 | −2.62 | −2.03 | 0.76 |
| 205609_at | ANGPT1 | angiopoietin 1 | 4.12E−02 | 0.54 | −2.20 | −3.11 | 0.73 |
| 202890_at | MAP7 | microtubule-associated protein 7 | 3.30E−02 | 0.62 | −2.30 | −2.31 | 0.73 |
| 203485_at | RTN1 | reticulon 1 | 2.60E−02 | 0.54 | −2.40 | −2.29 | 0.72 |

Spec = specificity,
FC = fold change,
AUC = area under the curve of Receiver Operator Characteristic Analysis,
negative t-statistic indicates gene is down in responders.

Whether increasing the number of genes in the classifier improved its predictive value was also examined. Using the LOOCV approach and then plotting sensitivity, specificity, and overall error rate of each classifier, the top gene alone was found to provide the best predictive value (data not shown). Adding genes to the classifier in a linear fashion did not improve its predictive value. Using a cutoff that biases for high sensitivity, the LOOCV demonstrated that the expression of the RASGRP1 gene allowed for a NPV 88.9%, and a PPV of 70.6%, with an overall predictive accuracy of 76.9% (FIG. 1A). In addition, Kaplan Meier analysis showed a significant difference in median overall survival of the responders (386 days) and those with progressive disease (68 days) (FIG. 1B). Over expression of this single gene therefore predicted response to tipifarnib in newly diagnosed AML with a high negative predictive value.

Identification of a Top Scoring Pair Classifier

Figure 2:
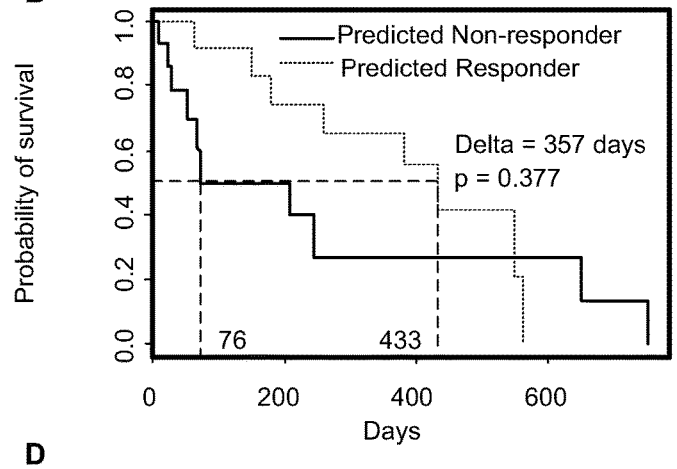
FIG. 2 depicts the performance of the RASGRP1:APTX gene pair as a predictor of response to tipifarnib in AML. The overall survival of newly diagnosed AML patients (A) and relapsed/refractory AML patients (C) stratified with the 2-gene classifier are plotted using Kaplan-Meier analysis. The accuracy rates of the two-gene classifier in newly diagnosed AML (B) and relapsed/refractory AML (D) are shown.
Figure 2:
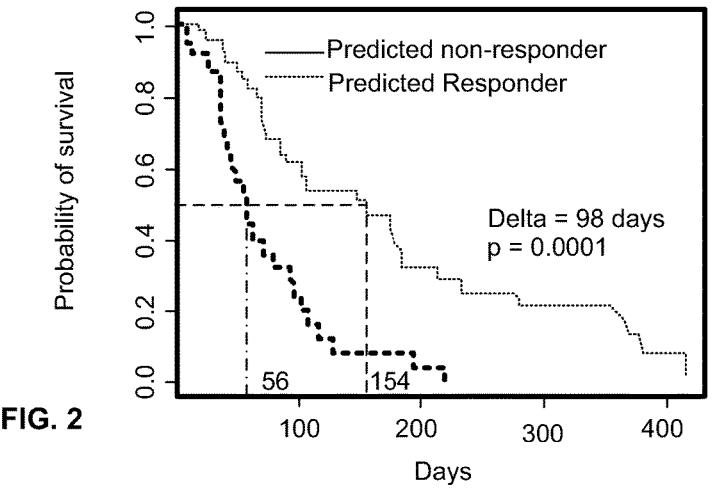

The predictive value of RASGRP1 was not improved if additional genes were added to the classifier using a linear approach. An alternative gene selection algorithm was utilized to select genes that would improve the predictive value of RASGRP1 alone. To this end the Top Scoring Pair (TSP) algorithm was utilized to identify the best pair of genes that would provide the greatest predictive accuracy. Geman et al. (2004). This approach was utilized to exploit the greatest difference in expression between two genes and may be useful when aiming to develop a qPCR based diagnostic assay. The TSP from the training set was RASGRP1 and aprataxin (APTX). RASGRP1 and APTX were over- and under-expressed in responders, respectively. A robust LOOCV showed that this top scoring pair (TSP) provided 85.7% NPV and 91.7% PPV in the training set of samples with an overall error rate of only 8% (FIG. 2A). The difference in overall survival between predicted responders and non-responders was 357 days (FIG. 2B). These data demonstrate that the model-building algorithm has a low associated prediction error rate.

Figure 3:
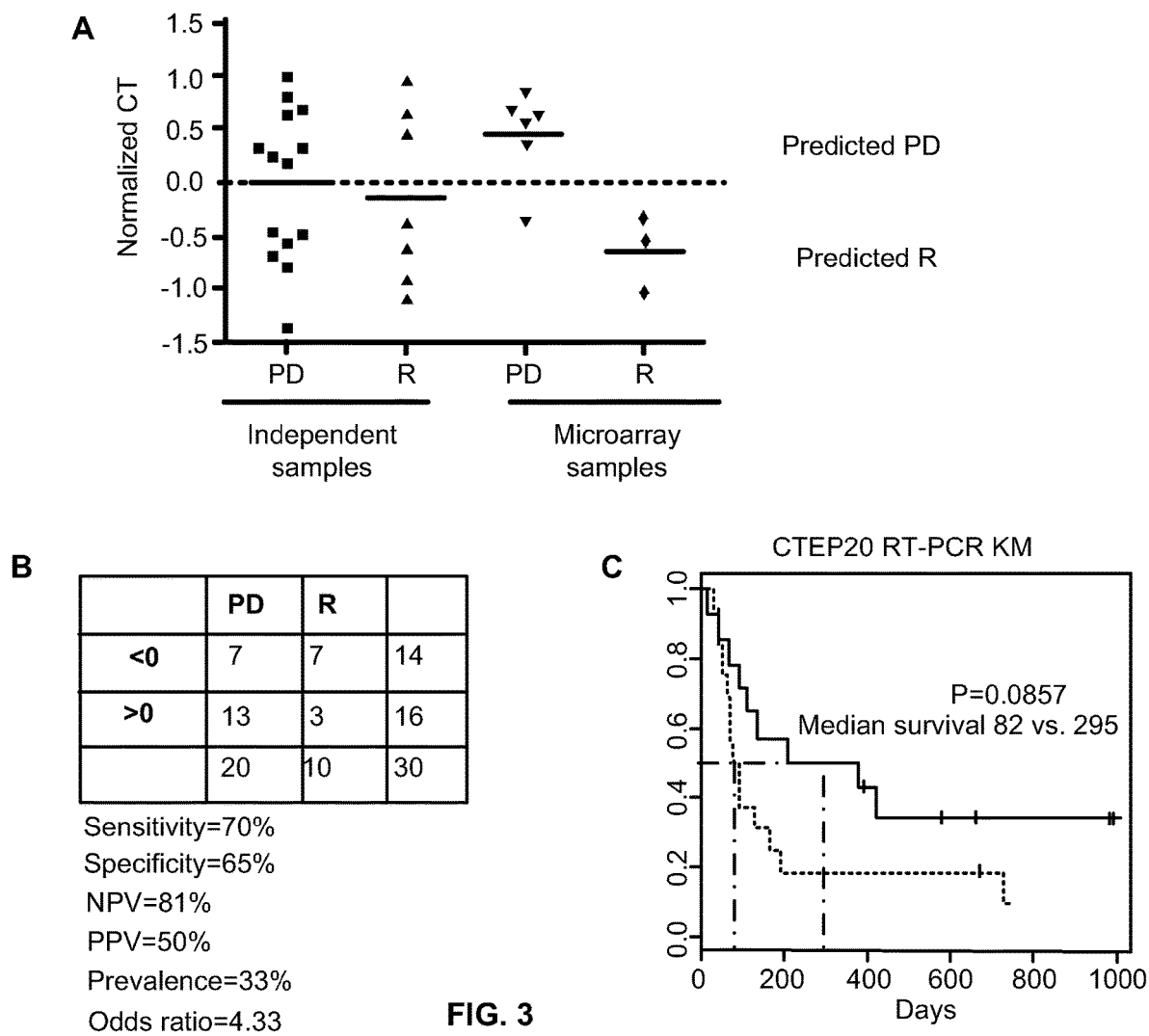
FIG. 3 depicts the performance of RASGRP1:APTX gene classifier using qPCR. (A) The normalized RASGRP1:APTX Ct values for 20 responders and 10 patients with progressive disease. The 20 independent samples and 10 training samples that were run on microarray are shown separately. Horizontal bars indicate group means. (B) The accuracy rates of the RASGRP1 gene classifier in newly diagnosed AML for all 30 patients are shown using a cutoff of 0 was used to stratify patients. (C) The associated overall survival of the stratified patients are plotted using Kaplan-Meier analysis.
Figure 4:
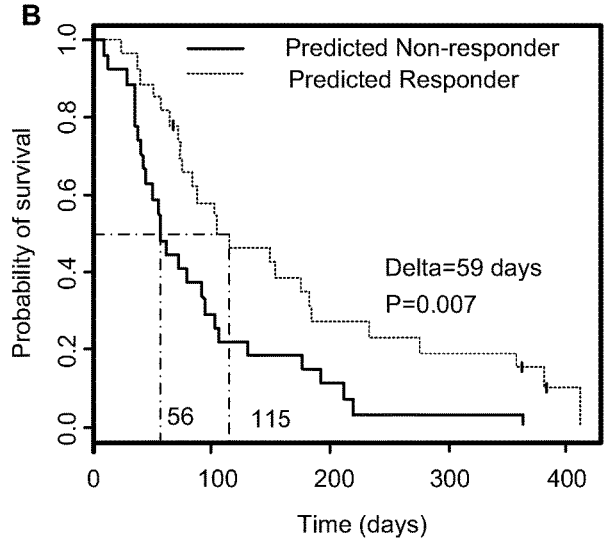
FIG. 4 depicts the performance of the RASGRP1 gene as a predictor of response to tipifarnib in relapsed and refractory AML. The accuracy rates (A) and Kaplan Meier survival curves (B) using the RASGRP1 gene classifier in relapsed/refractory AML.

Validation of the RASGRP1:APTX Classifier in an Independent Set of Relapsed or Refractory AML External validation of the TSP classifier was performed in an independent microarray dataset comprising of 54 relapsed/refractory AML patient samples. A diagnostic assay that predicts likely response to a cancer therapy should have a high sensitivity (and negative predictive value) since it is important to capture as many potential responders as possible. Therefore, to define an appropriate cutoff for testing the TSP classifier the need to obtain a high sensitivity of predicting responders while maintaining an acceptable level of specificity was considered. In the training set, the level of specificity that could be achieved ranged from approximately 30% to 100% when the sensitivity was set at 100% to 80%, respectively. To ensure the classifier would predict as many responders as possible a conservative cutoff that provided a specificity of approximately 60% in the training set was tested. When this cutoff was applied to the independent testing set of relapsed/refractory AML, the RASGRP1:APTX gene classifier stratified responders with 92% NPV and 27.6% PPV (compared to 18.5% prevalence) (FIG. 3C). The associated odds ratio for being a responder was 4.38. While this was similar to the predictive accuracy of RASGRP1 alone, the application of the TSP classifier demonstrated a better NPV and an improved difference in overall survival of 98 days between predicted responders and progressors (FIG. 3A), compared to only 56 days for RASGRP1 (FIG. 4).

QPCR Validation of the RASGRP1:APTX Expression Ratio

A two-gene expression ratio allows the use of a more clinically relevant qPCR detection system. Thirty samples (20 PD, 6 CR, 3 HI and 1 PR) provided enough total RNA for qPCR. Therefore, the RASGRP1:APTX gene expression ratio was evaluated as a predictor of response to tipifarnib using TaqMan® qPCR in these 30 samples (10 responders, 20 progressive disease) from the newly diagnosed AML clinical study. Nine of these samples had been assayed on the microarray platform, however 21 had not been utilized in the discovery set due to poor quality RNA. Therefore, two thirds of this test set was comprised of completely independent samples.

Evaluation of the 9 samples indicated there was good correlation (r=0.74) of the RASGRP1:APTX expression ratio between the two platforms (FIG. 6). Using a cut-point of 0, the two-gene classifier correctly predicted the treatment outcome in 20 of the 30 patients with PPV and NPV of 50% and 81%, respectively (FIG. 3B). The median overall survival of the predicted resistant patients was 82 days while those classified as responders had a median value of 295 days (FIG. 3C).

Figure 5:
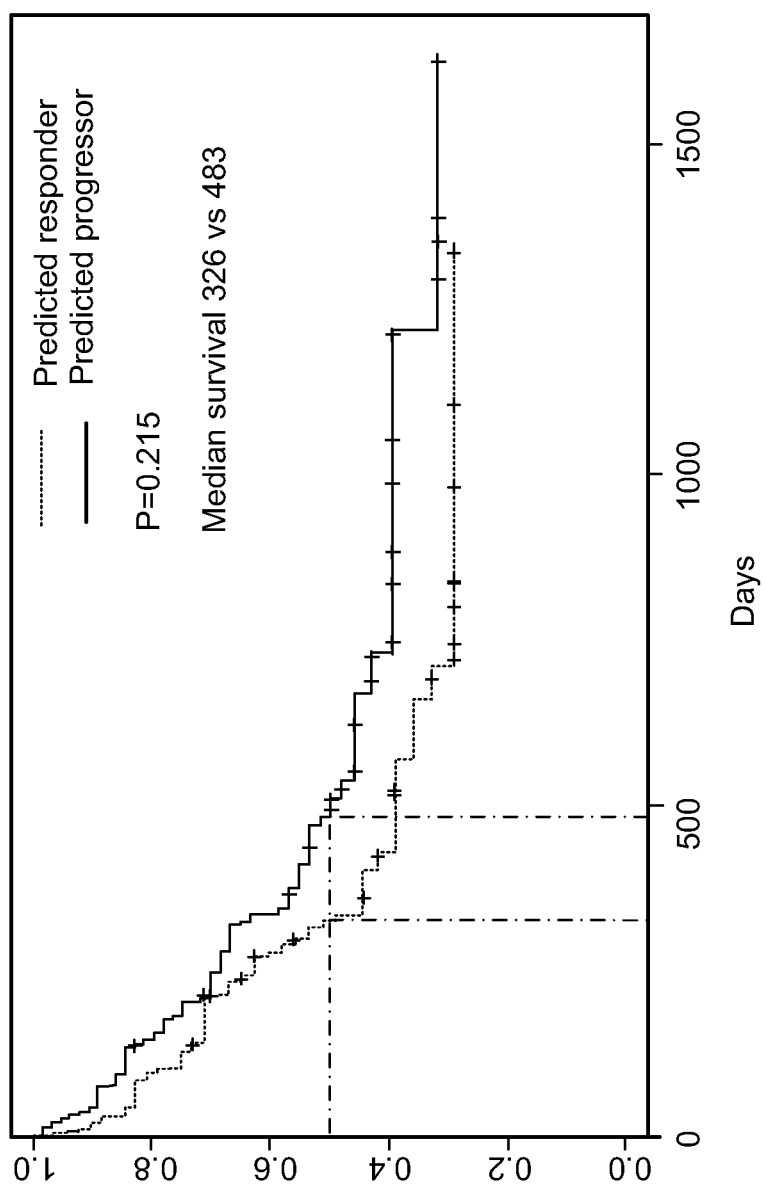
FIG. 5 depicts the overall survival of non-FTI treated AML patients stratified with the RASGRP1:APTX gene expression ratio. Three cDNA probes for both RASGRP1 and APTX were present in the available data set. We first calculated the mean value for each gene and then calculated the RASGRP1:APTX ratio of these values. Patients whose ratio was above 1 were classified as progressors and those with a ratio below 1 were classified as responders. Kaplan-Meier analysis was then performed.

The RASGRP1:APTX Classifier does not have Prognostic Utility Independent of FTI Treatment The two-gene expression ratio was tested in an independent microarray dataset of 116 AML patients treated with chemotherapeutic regimes. When the RASGRP1:APTX classifier was applied to this set of patients, utilizing a similar cut-off as for the tipifarnib-treated population, no significant separation in overall survival was seen (FIG. 5). Nor were significant survival differences observed when a range of other cut-offs was utilized (Table 4). This indicated that the RASGRP1:APTX classifier specifically stratifies patients who have been treated with tipifarnib and is not relevant to non-FTIs. On the other hand when the prognostic signature was applied to our set of relapsed and refractory AML patients there was a clear stratification in terms of overall survival.

TABLE 4

| cutoff | p value | Responders median OS | Progressors median OS | No. Responders | No. Progressors |
|---|---|---|---|---|---|
| 0.5 | 0.956 | 336 | 414 | 13 | 103 |
| 0.6 | 0.342 | 672 | 374 | 24 | 92 |
| 0.7 | 0.266 | 511 | 335 | 34 | 82 |
| 0.8 | 0.269 | 511 | 326 | 47 | 69 |
| 0.9 | 0.101 | 540 | 316 | 57 | 59 |
| 1 | 0.215 | 483 | 326 | 64 | 52 |
| 2 | 0.795 | 374 | 570 | 94 | 22 |
| 3 | 0.209 | 346 | 909 | 104 | 12 |

OS = overall survival

Example 2

This example describes an improved RT-PCR assay suitable for applying the two-gene assay to FTI combination therapy. During the analytical assay development Taqman assays for 3 markers: RASGRP1 (guanine nucleotide exchange factor that activates RAS), APTX (aprataxin involved in DNA excision repair) and HMBS (used as an internal control) were designed. HMBS could be used as a control in an embodiment or be dispensed with in other embodiments. Sequences of Taqman primer probe sets and their amplicons are listed above in the Summary section and in the Sequences Section of this disclosure. Namely, for APTX-SEQ #3-4 and 2, RASGRP1 primer probe set SEQ #56 and 1; and HMBS-SEQ #7-9.

Quantitative RT-PCR assays were developed and optimized using ABI-7500 platform to assess the 2-gene ratio performance with FAM-labeled RASGRP1, Gold 540-APTX and Cy5-HMBS in a single-tube triplex format. JY cellular RNA and Universal RNA (Stratagene) were used as external normalization.

RASGRP1:APTX ratio=$2^{\wedge}-((A-B)-(C-D))$

Where
  A: Sample RASGRP1 Ct value
  B: JY (or Universal) RNA (+) RasGRP1 Ct value
  C: Sample APTX Ct Value
  D: JY (or Universal) RNA (+) APTX Ct Value Other sources of cellular RNA could be substituted provided the assay parameters, in particular, the threshold, are recalculated for the particular cellular RNA employed for external normalization. The reference RNA used for external normalization is preferably from a cell line grown under defined conditions and that is relatively non-responsive to FTIs. Without being bound by theory, a suitable reference RNA may be derived from a cell line that is neutral in its response to FTI. Such a reference cell line may be developed from patients testing in the threshold region based on the two-gene assay, but who actually are non-responsive to FTI treatment. Thus, without being bound by theory, such patients are a likely source for developing an improved reference RNA for the two-gene ratio test. One possible method for developing and evaluating a cell line may be to select a cell line that, when used as an external control in the two-gene assay, tends to increase the threshold. This criteria is reasonable because such a cell line(s) will damp (due to a possible correlation in its two-gene response and that being measured) the measured two-gene ratio the least. Alternatively, the external control may be selected using a defined combination of APTX and RASGRP1 RNA to allow for absolute quantitation or using AUC to maximize discrimination between responders and non-responders. The choice of the external control is not the only source of variability in the threshold employed in the two-gene assay.

Two RT-PCR formats were developed and their performance assessed using a standard curve analysis. Both formats are demonstrably equivalent in performance with a high Pearson correlation using both raw $C_t$s of 3 markers and derived from them 2-gene ratio values ($R2=1-0.93$, $P<0.000$; Table 5).

TABLE 5

Pearson Correlation between RUO and GMP RT-PCR assays
RUO vs GMP RT-PCR format

| | |
|---|---|
| RasGRP1, Mean $C_t$ | 0.97 |
| APTX, Mean $C_t$ | 0.99 |
| HMBS, Mean $C_t$ | 1.00 |
| Ratio normalized to JY control RNA | 0.93 |

RUO format uses a commercially available RNA-to-Ct One Step RT-PCR Kit distributed by INVITROGEN® (Cat. No. 4392938). This format has a 20 µl reaction volume with 50 ng total RNA input according to the manufacturer's instructions.

GMP format is based on the VERIDEX® BLN RT-PCR Kit components (GeneSearch® Breast Lymph Node (BLN) Test Kit, IVD, Cat #2900004) with GeneSearch® BLN Enzyme Mix, IVD, P/N 7700040 and BLN Base Master Mix, P/N 7700031 used for preparation of RT-PCR master mix. The GMP format has a 25 µl reaction with 50 ng RNA input using an optimized RT step described next.

RT-PCR Multiplexed Protocol in a GMP Format 50 ng of total RNA was used as a target input in a triplex qRT-PCR which was carried out on an Applied Biosystems Prism 7500 Sequence Detection System in a 25 µL reaction. RNA samples (including normalization control RNAs) were thawed on ice and diluted to 10 ng/µl. The qRT-PCR was carried out using reagents from the VERIDEX® BLN RT-PCR Kit (GeneSearch® Breast Lymph Node (BLN) Test Kit, IVD, Cat #2900004): GeneSearch® BLN Enzyme Mix, IVD, P/N 7700040 and BLN Base Master Mix, P/N 7700031.

25× probe-primer master mix was prepared comprising: 400 nM SEQ No. 1 and 2, respectively, and 200 nM FAM-labeled RasGRP1 (SEQ No. 10); 400 nM SEQ No. 3 and 4, and 200 nM Gold 540-APTX (SEQ No. 11), and 400 nM of SEQ No. 8 and 9 and 200 nM Cy5-HMBS (SEQ No. 12) as summarized in Table 6.

TABLE 6

25X Probe/Primer Mix

| 3plex-1 (25X) Marker | Sequence | Stock to Add/rxn | 500 | Final Conc. in 25 µL |
|---|---|---|---|---|
| RASGRP1 | RASGRP1 SEQ ID NO: 5 | 0.10 | 50.00 | 0.4 µM |
| | RASGRP1 SEQ ID NO: 6 | 0.10 | 50.00 | 0.4 µM |
| | RASGRP1 (Fam) SEQ ID NO: 10 | 0.05 | 25.00 | 0.2 µM |
| APTX | APTX SEQ ID NO: 3 | 0.10 | 50.00 | 0.4 µM |
| | APTX SEQ ID NO: 4 | 0.10 | 50.00 | 0.4 µM |
| | APTX SEQ ID NO: 11 (Gold) | 0.05 | 25.00 | 0.2 µM |
| HMBS | HMBS SEQ ID NO: 8 | 0.10 | 50.00 | 0.4 µM |
| | HMBS SEQ ID NO: 9 | 0.10 | 50.00 | 0.4 µM |
| | HMBS SEQ ID NO: 12 | 0.05 | 25.00 | 0.2 µM |
| | idTe | 0.25 | 125.00 | |
| | Total | 1.00 | 500.00 | |

Each reaction consisted of 9 µL of BLN Base Master Mix, 10 µL of 2.5×BLN Enzyme mix and 1 µl of 25× primer/probe mix. The primer/probe mix had a final concentration of 400 nM of forward and reverse primers and 200 nM of fluorescent probes for each marker. 5 µl of total RNA from patient samples or normalization controls (Universal or JY RNA) was added to 20 µl of RT-PC master mix.

A threshold/cutoff of 5.2 was determined based on JY cellular RNA used as an external normalization control.

The qRT-PCR assays were carried out using the following cycling parameters: 1 min at 95° C. for denaturation step; 30 minutes at 58° C. (RT reaction); 5% ramp to 70° C. and incubation for 2 min followed by 40 cycles at 95° C. for 15 seconds (denaturation) and 60° C. for 1 minute (annealing/extension). This optimization of probe-primer concentrations of the GMP RT-PCR format in a single-tube multiplexed set-up attained a robust and sensitive detection of RNA targets from both bone marrow and peripheral blood samples at the level of 0.6 ng with Ct values around 31, i.e. in a low variability and highly reproducibility range of Cts (FIG. 3). This reaction format is suitable for commercialization of the test, being based on the GMP grade reagents formulated and manufactured for the FDA-approved BLN kit, such as Tth Polymerase (enzyme mix) and Base master mix. Some details for the Master Mix based protocol are provided in Table 7.

TABLE 7

Master Mix based protocol
Reagents
BLN Enzyme mix, BLN Master Mix
Prepare bulk RT-PCR Master Mix
Master Mix

| RT-PCR | 1 rxn. (µL) |
|---|---|
| BLN Base Master Mix | 9 |
| 2.5X BLN Enzyme Mix | 10 |
| 25X Primer/Probe mix | 1 |
| Total | 20 |

Prepare bulk RT-PCR Mix by multiplying reagent volumes on the table by the number of Samples plus exra 10%
Add 20 µL Master Mix in each well of a 96-well plate

TABLE 7-continued

Master Mix based protocol
Reagents
BLN Enzyme mix, BLN Master Mix
Prepare bulk RT-PCR Master Mix
Master Mix

| RT-PCR | 1 rxn. (µL) |
|---|---|

Add 5 µL diluted RNA sample to appropriate well
Add 5 µL of Universal RNA (external control) and (Nf water—No Target Control)
Seal the plate. Vortex briefly and centrifuge at 1500 rpm for 1 min.
Place in ABI 7500(1)

Data Analysis
  1. Inclusion Criteria
  The cycle threshold (Ct) values obtained from ABI7500 data output files were used for data analysis. $C_t$ Cutoffs for "No Test" for each Marker were selected as follows:
HMBS (internal control maker) Ct should not be greater than 30;
RASGRP1 $C_t$—not greater than 35 and
APTX $C_t$—not greater than 35.
  If a sample had any one of the two markers, RASGRP1 or APTX, above the $C_t$ cutoff level, it was considered as "No Test" (excluded from the data analysis). Results presented in Table 8 demonstrate equivalency between singlex and triplex (single-tube) formats of RT-PCR set-up when comparing slope values and PCR efficiency. Table 9 presents further improvements by extending RT step to 30 minutes.

TABLE 8

Performance of Singlex vs. Triplex RT-PCR formats

| | PCR QC | RASGRP1-Fam | APTX-Gold | HMBS-Cy5 |
|---|---|---|---|---|
| Triplex RT-PCR | Slope | −3.6 | −3.6 | −3.6 |
| | Y-Intercept | 29.5 | 29.6 | 29.5 |
| | Efficiency | 91% | 90% | 91% |
| Singlex RT-PCR in 3 channels | Slope | −3.5 | −3.6 | −3.6 |
| | Y-Intercept | 30.0 | 29.8 | 29.6 |
| | Efficiency | 92% | 89% | 89% |

TABLE 9

Triplex RT-PCR Performance Optimization
30 min RT, Primers-400 nM, Probes 200 nM

| Target ng input | Marker | Average Ct | PCR Efficiency | |
|---|---|---|---|---|
| 100 | RasGRP1-Fam | 24.0 | Slope | −3.4 |
| 50 | | 25.1 | Intercept | 30.8 |
| 25 | | 25.9 | Efficiency | 95% |
| 12.5 | | 26.9 | | |
| 6.25 | | 28.2 | | |
| gDNA(8 ng) | | Undetermined | | |
| NTC | | Undetermined | | |
| 100 | APTX-Gold | 23.7 | Slope | −3.3 |
| 50 | | 24.7 | Intercept | 30.2 |
| 25 | | 25.6 | Efficiency | 102% |
| 12.5 | | 26.5 | | |
| 6.25 | | 27.7 | | |
| gDNA(8 ng) | | Undetermined | | |
| NTC | | Undetermined | | |
| 100 | HMBS-Cy5 | 22.6 | Slope | −3.3 |
| 50 | | 23.5 | Intercept | 29.1 |
| 25 | | 24.4 | Efficiency | 100% |
| 12.5 | | 25.4 | | |
| 6.25 | | 26.7 | | |
| gDNA(8 ng) | | 35.8 | | |
| NTC | | Undetermined | | |

Using GMP RT-PCR format, Universal RNA (from AGILENT™) and JY RNA controls (from in-house cultured cell line) were run in RT-PCR with 37 patient samples from Phase 2 T+E study. This analysis was later repeated with 40 patient samples. Both analysis, based on the outcome of ROC curve analysis, are presented in Table 10, to show that the assay performance is equivalent when using JY or Universal RNA controls for raw $C_t$ normalization with an adjustment to the threshold.

The use of Universal RNA as the external control resulted in a threshold of 7.3 compared to a threshold of 5.2 when JY RNA was used as the external control. In these threshold determinations, the calculations treated CR as the Response criteria—with all other response types treated as non-responsive.

TABLE 10

ROC Curve Analysis: CR vs. NR for TthPol GMP RT-PCR format

| Normalization Control | AUC | SE | 95% CI | Cutoff by ROC analysis | Sensitivity | 95% CI | Specificity | 95% CI | Sample number |
|---|---|---|---|---|---|---|---|---|---|
| JY RNA (37 patient analysis) | 0.8 | 0.97 | 0.629 to 0.908 | >5.2 | 66.67 | 30.1 to 92.1 | 92.86 | 76..5 to 98.9 | CR = 9 NR = 28 |
| Universal RNA (37 patient analysis) | 0.8 | 0.97 | 0.629 to 0.908 | >5.2 | 66.67 | 30.1 to 92.1 | 92.86 | 76..5 to 98.9 | CR = 9 NR = 28 |
| JY RNA (40 patient analysis) | 0.8 | 0.0881 | 0.636 to 0.904 | >5.2 | 63.64 | 30.9 to 88.8 | 93.1 | 77.2 to 99.0 | CR = 11 NR = 29 |
| Universal RNA (40 patient analysis) | 0.8 | 0.0881 | 0.636 to 0.904 | >7.3 | 63.64 | 30.9 to 88.8 | 93.1 | 77.2 to 99.0 | CR = 11 NR = 29 |

Although the threshold in the 2-gene assay is dimensionless (being the ratio of RASGRP1 and APTX), without being bound by theory, it is believed that the threshold value may depend on the standards conditions and the reagents used. Therefore, it is preferable to specify the threshold relative to a performance based criterion, such as a ROC curve based criterion. Thus, the threshold/cutoff may be adjusted to meet other requirements such as keeping the AUC value constant with a change in the external control. In this case, using Universal RNA instead of JY RNA as the external control resulted in a higher threshold/cutoff of 7.3 with AUC remaining unchanged.

Example 3

This example shows the two-gene assay is effective in newly diagnosed AML patients. The 2-gene response predictive assay was tested first on leukemic blasts from a subset of 84 newly diagnosed AML patients enrolled in Phase 1 dosing study of tipifarnib and etoposide using the technical RT-PCR protocol described in Blood 2008, 111: 2589. The clinical plan of Phase 1 trial is described in Blood 2009, 113:4841.

Briefly, fifty-one (51) unpublished evaluable patient samples from this study were analyzed for a preliminary assessment of the performance of the 2-gene assay. Table 11 summarizes the results using a threshold of 5 with RR standing for the response rate with responders exhibiting CR or PR, PPV for positive predictive value and NPV for the negative predictive value. 13 out of 51 patients responded for an RR of about 0.25. Among those who exceeded the threshold of 5 of the two-gene assay, half (9 out of 18) responded resulting in a PPV of about 0.5. Of the patients who did not exceed the threshold, 29 out of 33 did not respond leading to a NPV of 0.88.

TABLE 11

Results of the two-gene assay on 51 patients

|      | CR/PR | Remainder | Total | Measure | Measure Value |
|------|-------|-----------|-------|---------|---------------|
| >5   | 9     | 9         | 18    | RR      | 0.25          |
| 5<   | 4     | 29        | 33    | PPV     | 0.5           |
| Total| 13    | 38        | 51    | NPV     | 0.88          |

Compare RUO and GMP RT-PCR Formats

Using both RUO and optimized GMP RT-PCR formats gene expression profiles from 33 bone marrow samples from newly diagnosed AML patients evaluable for clinical response were analyzed. One patient sample (HI) from the RUO RT-PCR data set didn't meet analysis inclusion criteria, thus was excluded from both data sets. Patient annotations by best response are presented in Table 12.

TABLE 12

Breakdown of Responders and Non-responders

| Best Response | Number of Patients |
|---------------|--------------------|
| PD            | 17                 |
| SD            | 3                  |
| CR            | 7                  |
| PR            | 4                  |
| HI            | 1                  |
| Total Evaluable Patients | 32       |

At a later date corresponding, the 33 patients were analyzed again and were found to have 7 complete remission (CR), 4 HI, 3 PR, 7 PD and 11 SD cases (Table 13). When using CR as response criteria, 7 patients were classified as Responders and 25 as Non-responders while when using CR/PR/HI as response criteria, 12 patients were classified as Responders and 20 as Non-responders.

TABLE 13

Breakdown of Responders and Non-responders

| Best Response | Number of Patients |
|---------------|--------------------|
| PD            | 7                  |
| SD            | 11                 |
| CR            | 7                  |
| PR            | 3                  |
| HI            | 4                  |
| Total Evaluable Patients | 32       |

A preliminary statistical analysis to evaluate a possible cutoff value separating 'normal' (Responders, R) from 'abnormal' (Non-Responders, NR) test results was carried out with responders being patients exhibiting CR, PR or HI A ROC curve analysis for both RT-PCR formats indicated almost equivalent assay performance with AUC value of the 2-gene ratio equal to 71% (Table 14). When using JY RNA as a normalization control the cutoff of 4.7 was determined for the RUO protocol and 5.2—for the GMP format based on the ROC curve analysis algorithm. Without being bound by theory, the difference in the thresholds and other parameters based on the format employed is believed to be, in part, due to the specificity or efficiency of the RT-PCR procedure and statistical fluctuations.

TABLE 14

Comparison of RUO and GMP formats
Table 14. Comparison of RUO and GMP formats

| RT-PCR FORMAT | 2-Gene Ratio Cutoff | Sensitivity | 95% CI | Specificity | 95% CI | AUC | NPV | PPV |
|---------------|---------------------|-------------|--------|-------------|--------|-----|-----|-----|
| ABI, RUO      | 4.7                 | 50%         | 21.2-78.8 | 90%      | 68.3 to 98.5 | 0.71 | 74% | 67% |
| VRX, GMP      | 5.2                 | 50%         | 21.2-78.8 | 95%      | 75.1 to 99.2 | 0.71 | 76% | 86% |

As in the case of the data presented in Tables 12 and 13, at the later date analysis, which treated responders as patients exhibiting complete remission (CR) only—PR and HI patients were included in the group of non-responders, led to the results in Table 15, which lead to thresholds of 5.1 corresponding to the RUO protocol and 5.2—corresponding to the GMP format based on the ROC curve analysis algorithm.

TABLE 15

Comparison of RUO and GMP formats

| RT-PCR Format | 2-Gene Ratio Cutoff | Sensitivity, % | 95% CI | Specificity, % | 95% CI | AUC | NPV, % | PPV, % |
|---|---|---|---|---|---|---|---|---|
| ABI, RUO | 5.1 | 85.7 | 42.2-97.6 | 80 | 59.3-93.1 | 0.83 | 95 | 55 |
| VRX, GMP | 5.2 | 71.4 | 29.3-95.5 | 92 | 73.9-98.8 | 0.83 | 92 | 71 |

When using a cutoff value of 5.2 for the GMP RT-PCR data set the overall response rate (for patients exhibiting CR or PR or HI) increased from 38% (ORR) to 86% (PPV) with a negative predictive value of 76% (Table 16) using JY RNA. In other words, 86% of the patients classified as responders by the two-gene assay actually responded, which is an improvement. This outcome is comparable to the 70% response expected from induction therapy in younger patients. In other words, 86% (6 out of seven patients) of those exhibiting a 2-gene ratio value of greater than 5.2 in the GMP RT-PCR format assay responded to treatment with a combination of tipifarnib and etoposide (which corresponds to a PPV of 86%). In contrast, 24% (six out of twenty-five patients) with a 2-gene ratio value of less than or equal to 5.2 responded to treatment with a combination of tipifarnib and etoposide, but were not detected with the 2-gene test. It should be noted that the threshold/cutoff may be adjusted to meet other requirements such as keeping the AUC value constant with a change in the external control. In this case, using Universal RNA instead of JY RNA as the external control resulted in a higher threshold/cutoff of about 8 (from about 5).

A later analysis treating responders as only exhibiting complete recovery led to

TABLE 17

Results using the GMP format with Responders defined by CR/PR/HI

| 2-Gene Ratio Cutoff | Responder R | Non-Responder R NR | Total | PPV | NPV | ORR | Sens | Spec |
|---|---|---|---|---|---|---|---|---|
| >5.2 | 5 | 2 | 7 | 71% | | | | |
| ≤5.2 | 2 | 23 | 25 | | 92% | | | |
| | 7 | 25 | 32 | | | 22% | 71.4% | 92% | the results in Table 17 showing superior NPV and higher sensitivity with comparable specificity.

Figure 8:
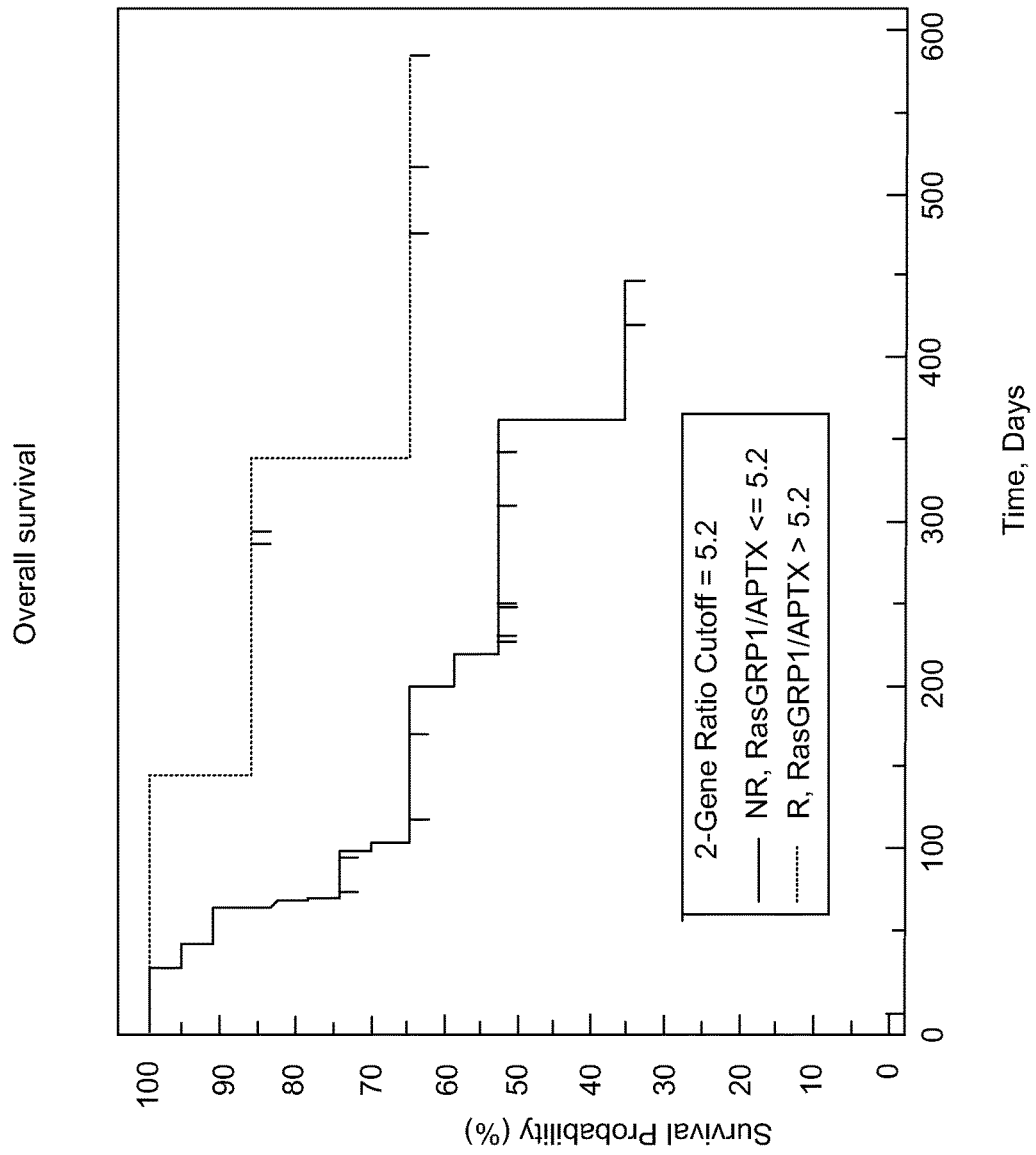
FIGS. 8 and 13 depict accuracy of the improved qPCR assay in a Phase 2 study of tipifarnib+etoposide study in elderly AML using Kaplan Meier analysis of patients stratified using an optimal ratio cutoff 5.2.
Figure 13:
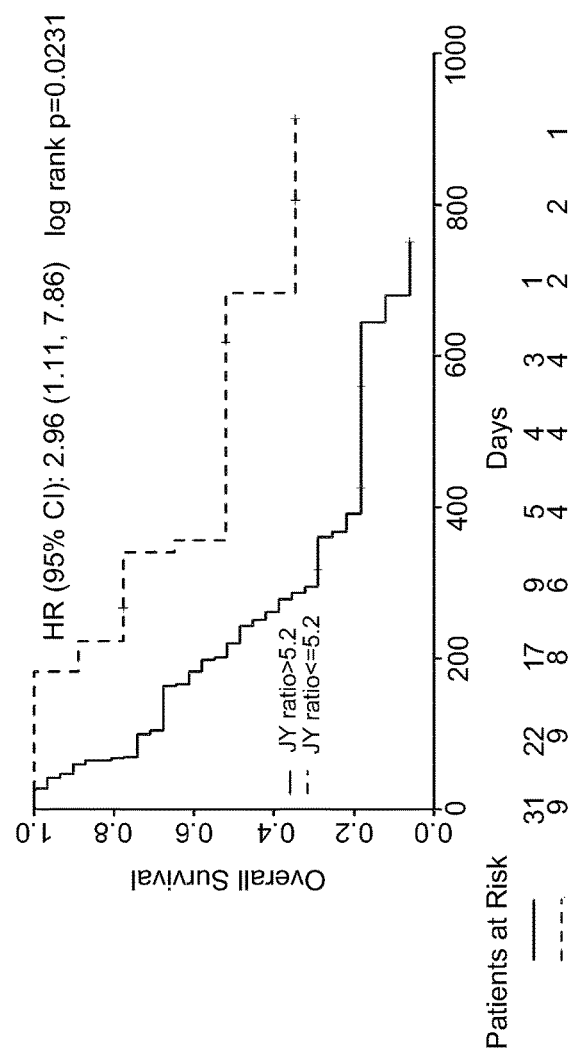

The Kaplan-Meier curve analysis with Hazard Ratio (HR) of 2.3 indicated a positive trend in favor of utility of a 2-gene ratio assay in predicting response between R and NR to the combination of tipifarnib and etoposide in elderly newly diagnosed AML patients (FIGS. 8 and 13—the two differ in the definitions used for identifying esponders). Based on the equivalency of the assay performance characteristics the GMP format was pursued for further development as a companion diagnostic assay.

TABLE 16

Results using the GMP format with Responders defined by CR/PR/HI

| 2-Gene Ratio Cutoff | Responder R | Non-Responder NR | Total | PPV | NPV | ORR | Spec | Sens |
|---|---|---|---|---|---|---|---|---|
| >5.2 | 6 | 1 | 7 | 86% | | | | |
| ≤5.2 | 6 | 19 | 25 | | 76% | | | |
| | 12 | 20 | 32 | | | 38% | 95% | 50% |

Further GMP RT-PCR Format Testing

Figure 9:
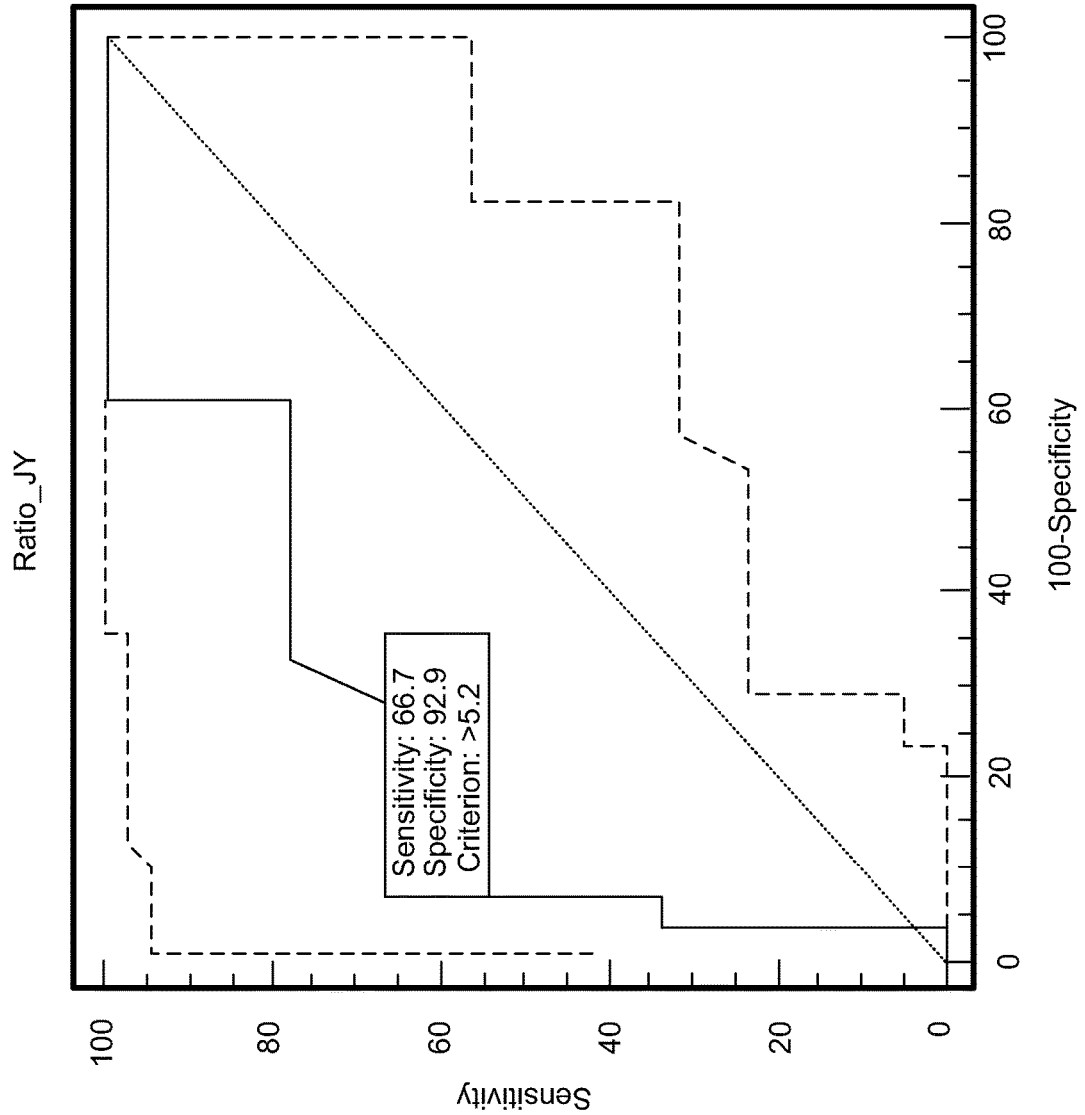
FIGS. 9 and 14 depict the ROC analysis indicating a discriminative value of the 2-gene ratio as 80% (AUC=0.80) for predicting overall response with a complete remission (CR) patient group used as the response criteria.
Figure 14:
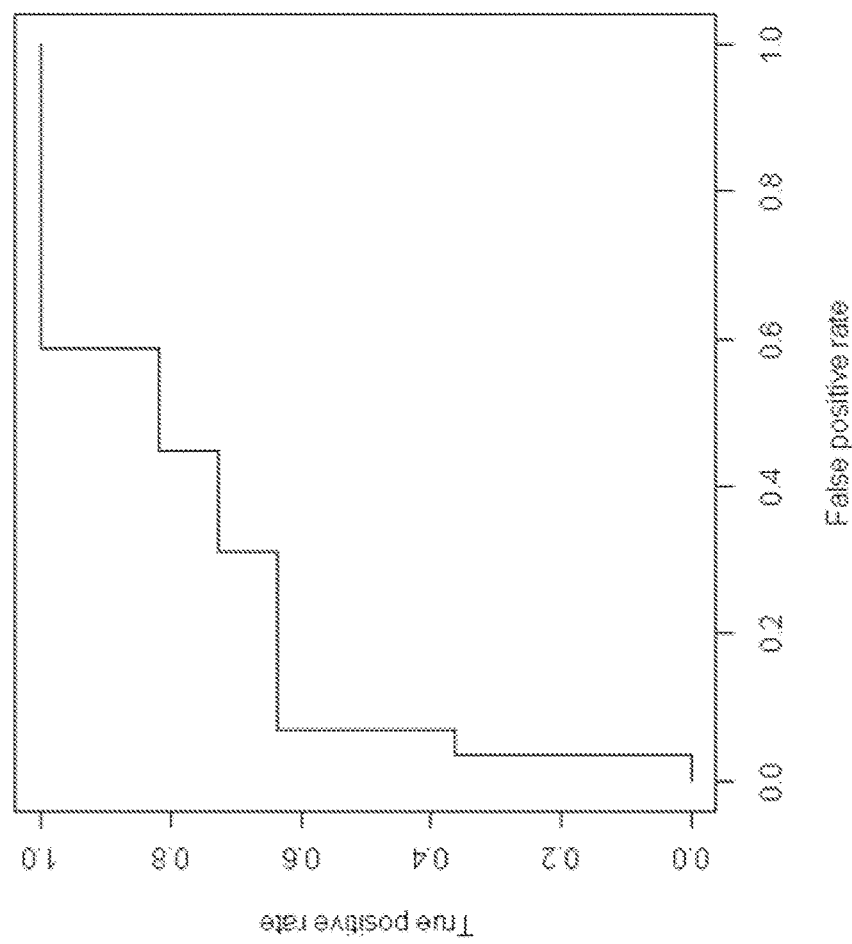

Following further improvements the single tube multiplexed RT-PCR assay in the GMP format was tested in 37 patients by adding 4 evaluable whole blood samples to the existing set of 33 bone marrow samples. Because bone marrow and whole blood samples generated equivalent raw Ct values for the three markers, they were merged in a single data set, which is summarized in Table 18. Receiver-operator characteristic (ROC) analysis indicated a discriminative value of the 2-gene ratio as 80% (AUC=0.80) for predicting overall response in a complete remission (CR) patient group used as response criteria corresponding to an overall response ORR (24%) computed as CR(9)/total patient n (37). This is illustrated in FIGS. 9 and 14. At the 2-gene ratio cutoff of 5.2 the assay sensitivity was 67% and specificity was 93%.

TABLE 18 merged data with results from whole blood and bone marrow samples

| Best Response | Patient Classification (J07901, baseline) | |
|---|---|---|
| NR | 19 | NR |
| SD | 3 | NR |
| CR | 9 | R |
| PR | 4 | NR |
| HI | 2 | NR |
| Total evaluable patients | 37 | 28 NR vs. 9 R |

With the definition of responders in Table 18, for the expanded patient set used in Table 18 the overall performance of the assay is described by Table 19.

Example 4

This example shows, consistent with prior examples that the two-gene assay is specific for treatments that comprise an FTI. The synergistic presence of another agent does not appreciably reduce the requirement for an FTI for the two-gene assay to be effective.

While it is plain that in an identifiable subset of patients suffering from AML, which is identified by the 2-gene assay, it is possible to effectively treat such patients with combination therapies comprising an FTI, like Zarnestra, it has been expected that in the absence of an FTI in the combination therapy, the 2-gene assay will not be helpful.

To empirically assess the specificity of the 2-gene assay, it was tested on 41 samples from AML patients not treated with the FTI, Zarnestra to see if the response correlated with the 2-gene assay results. These AML patients were treated with

TABLE 19

GMP format performance with CR the only response criterion

Figure 10:
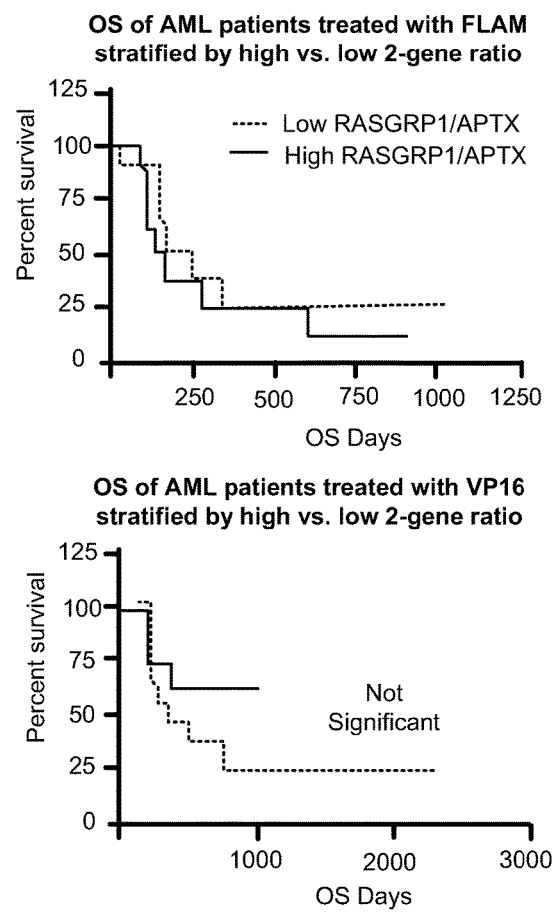
FIGS. 10 and 15 show there is no association between the 2-gene ratio and clinical response or overall survival in patients not treated with an FTI. Overall survival of 41 AML patients treated with intensive induction chemotherapy with ara-C, anthracycline, and a third agent (flavopiridol or etoposide): stratification by high vs. low 2-gene ratio.
Figure 10:
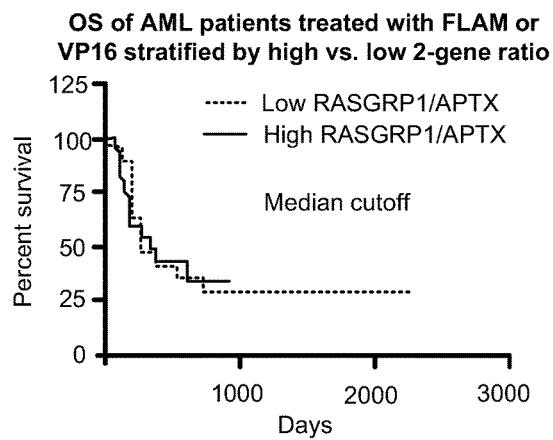

| 2-Gene Ratio Cutoff | Responder R | Non-Responder NR | Total | PPV | NPV | ORR | Spec | Sens |
|---|---|---|---|---|---|---|---|---|
| >5.2 | 6 | 2 | 8 | 75% | | | | |
| ≤5.2 | 3 | 26 | 29 | | 90% | | | |
| | 9 | 28 | 37 | | | 24% | 93% | 67% | traditional chemotherapeutic regimens consisting of ara-C, anthracyclines and VP16 (AcDVP16, n=23) and FLAM (n=18). FIG. 10 shows that there was no significant association between the 2-gene ratio and clinical response or overall survival. Thus, these results further confirmed that the 2-gene ratio assay does not predict response to therapy in non-FTI-treated AML patients. The ROC AUC was determined to be 0.5, which demonstrates no significant value in predicting clinical response to chemotherapeutic regimens that do not include an FTI.

Figure 15:
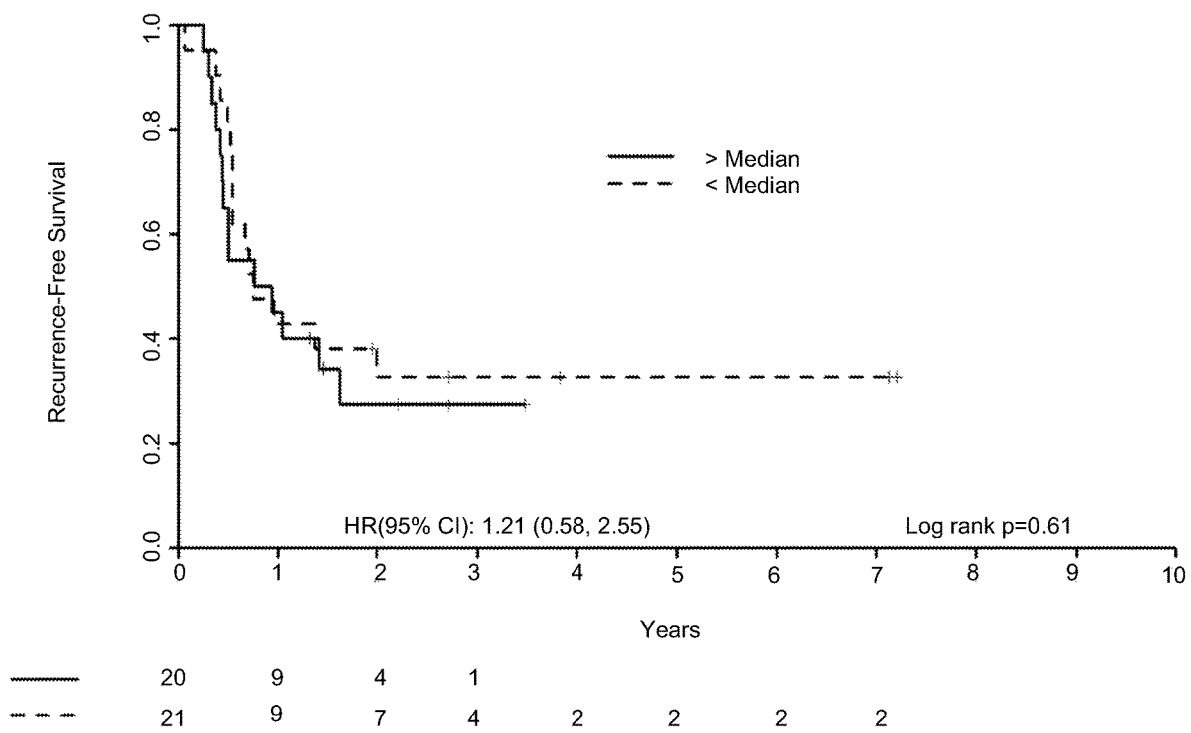

Furthermore, when subjects were classified as either high or low ratios based on the median of 2-gene ratio (0.959), 25th quantile (0.561), 75th quantile (1.248), there was no demonstrated benefit in overall survival. Following survival analyses were performed: 1) all patients, 2) VP16 only and 3) FLAM only. The results (FIGS. 10 and 15, all patients) showed there were no significant differences in overall survival (Days) between the two groups stratified by median ratio as well as in 2 sub-groups stratified by treatment regimen. This was also found to be the case when using cutpoints at the 25th and 75th quantile (data not shown).

Example 5

This example illustrates that not all sample collection techniques are equivalent. Excessive RNA degradation and other sources of variability dependent on the sample collection protocol can influence the two-gene assay.

The sample collection protocol typically requires the use of bone marrow samples in prior implementations of the two-gene assay. This is not only quite intrusive, but also painful for patients suffering from AML. The new protocol allows use of whole blood as is described in this example.

To identify a preferred sample collection protocol (sample type) for the assay equivalency testing study was performed between the two sample types (Bone Marrow vs. Whole Blood) using three (3) collection protocols (Paxgene system vs. a standard collection process in Heparin and EDTA tubes followed by a Ficoll-Paque centrifugation method), respectively. 11 AML patients provided by the Sidney Kimmel Comprehensive Cancer Center at Johns Hopkins University were tested.

Figure 11:
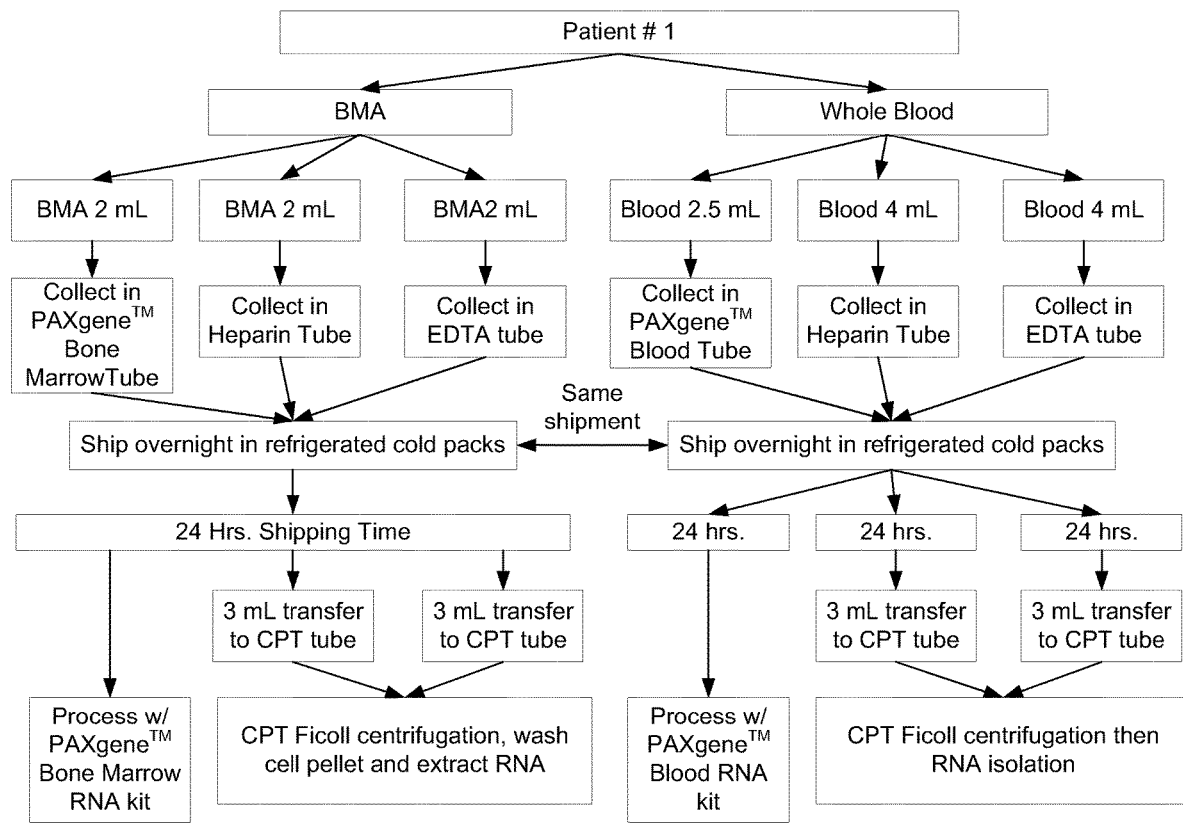
FIG. 11 depicts the work flow for comparing and determining the preferred sample collection problem.

Approximately 11 mL blood was drawn and 8-10 mL bone marrow was aspirated from each patient using 3 collection methods for each of 2 sample types according to the work flow depicted in FIG. 11. The following six protocols were tested according to this study design as depicted in FIG. 11:

Protocol 1: PAXgene™ Bone Marrow System Catalog No. 764114 (PreAnalytix, A QIAGEN/BD COMPANY). 2 mL volume of BMA was collected in PAXgene™ Bone Marrow tubes and shipped to VRX within 24 hrs at ambient temperature on refrigerated cold packs. RNA was isolated upon receipt of the samples using PAXgene Bone Marrow RNA kit (Cat. No. 764133).

Protocol 2: BMA collection was done in Sodium Heparin tubes (2 mL sample volume) and shipped to VRX within 24 hrs at ambient temp on refrigerated cold packs. Ficoll-Hypaque density gradient centrifugation step with direct freezing of cell pellets at −80 C and RNA extraction using Qiagen Blood Midi kit was performed at Veridex.

Protocol 3: BMA collection was done in EDTA tubes (2 mL sample volume) and shipped to VRX within 24 hrs at ambient temp on refrigerated cold packs. Ficoll-Hypaque density gradient centrifugation step with direct freezing of cell pellets at −80 C and RNA extraction using Qiagen® Blood Midi kit was performed at VERIDEX®.

Protocol 4: PAXgene™ Blood System. 2.5 mL blood was collected in PAXgene™ Blood tubes (Cat. no. 762165, PreAnalytix, A QIAGEN/BD COMPANY) and shipped to VRX within 24 hrs at ambient temp on refrigerated cold packs. RNA was isolated at Veridex upon receipt of the samples using PAXgene Blood RNA kit (Cat. no. 762164)

Protocol 5: Whole blood collected in Sodium Heparin tubes (4 mL Blood) was shipped to VRX within 24 hrs at ambient temp on refrigerated cold packs. Transfer of 3 mL blood to 4 mL CPT tube with subsequent Ficoll separation of mononuclear cells and direct freezing of cell pellets at −80 C was performed at Veridex. RNA extraction was performed using Qiagen Blood Midi kit.

Protocol 6: Whole blood collected in EDTA tubes (4 mL Blood) was shipped to VRX within 24 hrs at ambient temp on refrigerated cold packs. Transfer of 3 mL blood to 4 mL CPT tube with subsequent Ficoll separation of mononuclear cells and direct freezing of cell pellets at −80 C was performed at Veridex. RNA extraction was performed using Qiagen Blood Midi kit.

Based on the results from Agilent BioAnalyzer QC, PAXGene system use resulted in good quality RNA targets for both bone marrow and blood samples for all eleven patients compared to Heparin and EDTA protocols, most commonly used in clinical laboratory settings.

A direct method of RNA integrity assessment (RNA QC) is to run RNA on Agilent BioAnalyzer and calculate RIN values (RNA Integrity Number). As recommended by Qiagen using PAXgene system, RNA with RIN 7 and above (to 10) is considered a good-quality target. Please see an additional data in Table 17 with RIN values for the sample stability study with 11 patient samples. RIN values highlighted in yellow correspond to poor quality RNA samples (from Heparin and EDTA tubes). PAXgene system in comparison with the other 2 types of collection tubes generated only good quality RNA based on the evaluable by yield samples. In Table 20, NE stands for not evaluated; NA stands for not available; a RIN value of about 2 to 5 indicates degraded RNA; and a RIN value of about 5 to 7 indicates marginal RNA.

TABLE 20

Correlation by RIN values between sample collection/processing protocols

| | Agilent Profile (RIN) | | | | | |
|---|---|---|---|---|---|---|
| | Blood | | | Marrow | | |
| Sample ID | Heparin | EDTA | Paxgene | Heparin | EDTA | Paxgene |
| 1 | 10.0 | 10.0 | 8.7 | 9.7 | 9.6 | 9.0 |
| 2 | 9.0 | 9.2 | 8.9 | 6.6 | 7.2 | 8.9 |
| 3 | NE | NE | 9.4 | NE | 2.1 | 8.9 |
| 4 | 9.6 | 9.6 | NE | 7.9 | 9.3 | NE |
| 5 | 9.3 | 8.3 | 8.0 | 7.3 | 7.3 | 8.4 |
| 6 | 5.7 | 6.7 | 9.1 | 3.2 | 3.6 | 9.1 |
| 7 | NE | NE | 9.8 | NE | NE | NE |
| 8 | 3.4 | 2.9 | 9.1 | 2.6 | 2.4 | 9.6 |
| 9 | 4.9 | 3.9 | 9.4 | 8.6 | 8.4 | 8.1 |
| 10 | 9.3 | 9.2 | 9.9 | 9.6 | 8.9 | 9.8 |
| 11 | 7.7 | NA | 9.2 | 6.6 | 5.8 | 9.5 |

Samples marked NE were not analyzed for the insufficient sample yields after the sample prep step.

FIG. 12 (panels A and B) shows that bone marrow samples number 3 and 6 demonstrated substantial RNA degradation in Heparin tubes, which degradation elevated the values of 2-gene ratios. Raw Cts are inversely correlated with RIN values: for the lower RIN values the higher Cts are generated in all 3 channels in case of Heparin and EDTA protocols.

Figure 12A:
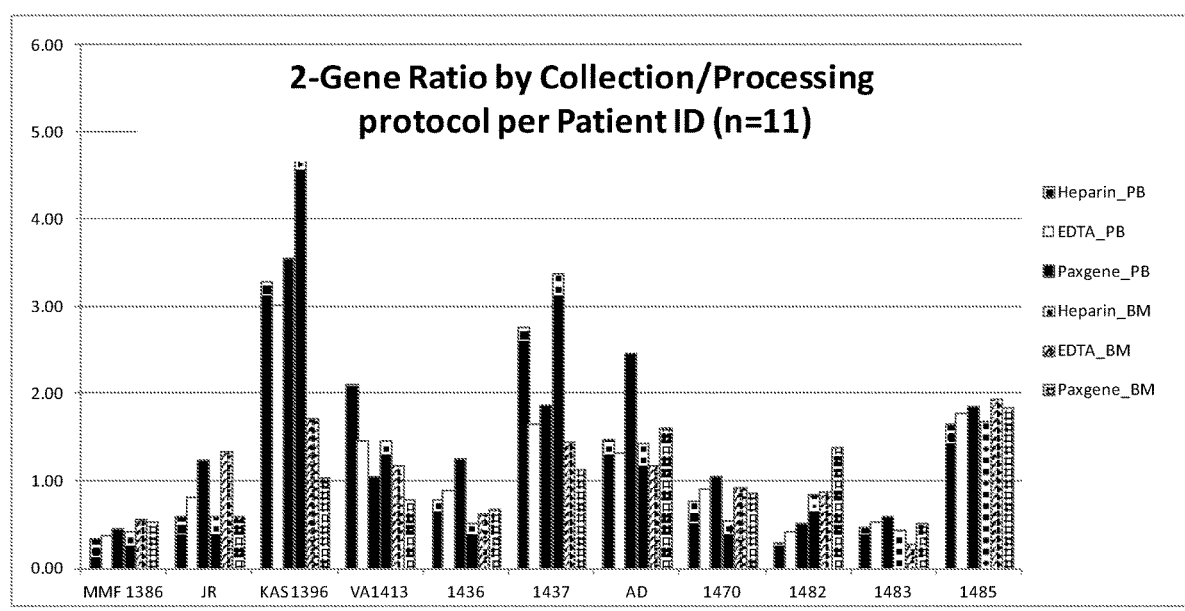
FIGS. 12A and 12B show the effect of the sample collection protocols on the result of the two-gene assay.
Figure 12B:
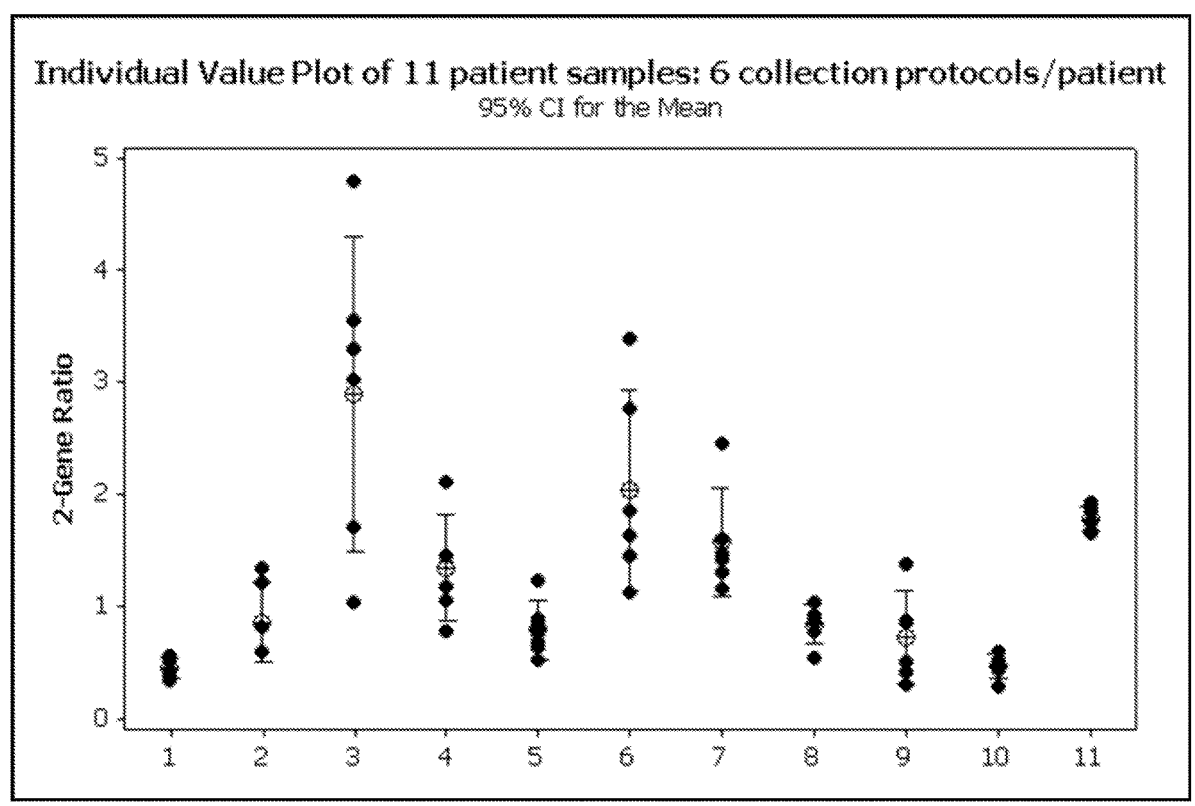

As is seen in FIGS. 12A and 12B, none of the samples exceed the threshold of 5 for the two-gene assay. The scatter in the measured two-gene ratio due to the collection protocol varies significantly as is FIG. 12B. Patients 3 and 6 appear to have the most scatter with the Heparin and Paxgene bone marrow collection protocols defining the two extreme boundaries for these patients. An examination of the data in TABLE 20 shows that the whole blood collection protocols correlate well with each other while the same cannot be said for the bone marrow collection protocols. Indeed, based on Table 20 and FIGS. 12A and 12B, it can be argued that the two-gene assay should preferably be performed using whole blood. To ensure consistency, the PAXgene PB protocol is preferred. Without being bound by theory, it is believed that RNA degradation might be more rapidly occurring in bone marrow samples than in whole blood, thus lower level of correlation is demonstrated between EDTA (Heparin) tubes and PAXgene system.

Further, collection of bone marrow samples in heparin tubes appears to less reliable than other methods, a detail that should improve sample collection procedures in general for assays other than for just the two-gene assay disclosed here.

Pearson correlation coefficients (R2) and p-values for bone marrow (BM) and blood samples (PB) with the six (6) collection/processing protocols of FIG. 11 are presented in Table 21. There is a good correlation observed between two-gene ratios for RNA samples obtained from Heparin, EDTA and PAXGene tubes in case of blood samples (values highlighted in red). However, there is a poor correlation observed between PAXGene bone marrow samples and other collection procedures. This observation is consistent with the lack of stabilization in Heparin tubes resulting in instability of RNA templates when bone marrow specimens are stored (shipped) under ambient conditions within 24 hrs before processing. These observations also support that PAXGene Whole Blood system as one of the preferred collection/processing protocols of this disclosure in view of the observed RNA integrity and reliability of 2-gene ratio values in such samples.

TABLE 21

Pearson correlation between sample collection/processing protocols

| | Heparin PB | Heparin BM | EDTA PB | EDTA BM | Paxgene PB |
|---|---|---|---|---|---|
| Heparin BM | 0.936 | | | | |
| p-value | 0 | | | | |
| EDTA BM | 0.933 | 0.913 | | | |
| p-value | 0 | 0 | | | |
| EDTA PB | 0.714 | 0.683 | 0.784 | | |
| p-value | 0.014 | 0.02 | 0.004 | | |
| Paxgene PB | 0.816 | 0.839 | 0.917 | 0.717 | |
| p-value | 0.002 | 0.001 | 0 | 0.013 | |
| Paxgene BM | 0.323 | 0.329 | 0.383 | 0.635 | 0.453 |
| p-value | 0.333 | 0.323 | 0.246 | 0.036 | 0.162 |

Example 6

This example, based in part on the patients described previously as part of Example 3, illustrates the adjustment of the tipifarnib dose to balance the toxicity with effective treatment of the patients with the aid of the two-gene assay to direct FTI combination therapy. This later analysis, performed in the context of determining better dosing strategies for tipifarnib and etoposide, also modified the analysis relating to RUO and GMP RT-PCR formats by treating CR as Responders, the rest being non-responders. The results of this later analysis have been presented in earlier described Examples.

Discussion

Stratification of patient populations to predict therapeutic response is becoming increasingly valuable in the clinical management of cancer patients. For example, companion diagnostics are required for the stratification of patients who are candidates for targeted therapies such as trastuzumab (Herceptin, Genentech) in metastatic breast cancer, and cetuximab (Erbitux, Merck) in colorectal cancer to provide quality care. Predictive biomarkers are also being utilized for imatinib (Gleevec, Novartis) in gastrointestinal stromal tumors, and for erlotinib (Tarceva, OSI Pharmaceuticals) and gefitinib (Iressa, Astra-Zeneca) in lung cancer. Currently there is no method available to predict response to a combination therapy that includes an FTI.

RASGRP1 was identified as the most robust single predictive gene expression marker with an overall predictive accuracy of 77% in the cross-validated training set for treatment with just an FTI. RASGRP1 is a guanine nucleotide exchange factor (GEF) that specifically activates RAS. Expression of RASGRP1 has been found in brain, T-cells, cells of monocytic lineage, and primitive hematopoietic precursors.

This disclosure provides the ratio of expression of RASGRP1 and APTX as a robust predictor of response to FTI combination therapy. This two-gene classifier showed predictive utility in the discovery set of newly diagnosed AML.

The disclosed simple qPCR-based diagnostic assay has wider utility in the clinic than gene expression microarrays due to its ability to assay poor quality clinical samples that may not be profiled by current microarray technologies. Further, the assay can detect a signal in whole blood samples instead of requiring bone marrow cells. The methodology for selecting an external control for the assay, a simpler calculation of the ratio based on the sample, the external control and just RASGRP1 and APTX makes it possible to offer patients, particularly elderly patients, the two-gene assay to determine whether a FTI combination therapy will assist them in fighting off AML.

The disclosed retrospective analysis of bone marrow aspirates collected in the context of the current tipifarnib+etoposide trial validate the 2-gene signature as a reproducible predictor of response to tipifarnib. The analysis also suggest that it is possible to prospectively discriminate those patients with AML who are likely to respond to tipifarnib vs. those who are not. The data substantiate the notion that the 2-gene signature is relatively specific for tipifarnib (or a farnesyl transferase inhibitor), since there appeared to be no predictive relationship between the RASGRP1:APTX mRNA ratio and two intensive investigational chemotherapy regimens, each of which included ara-C and an anthracycline with a third agent (flavopiridol or etoposide). Although the positive predictive value of the test in the context of the tipifarnib+etoposide Phase II trial was 78%, the negative predictive value (NPV) of the test was slightly lower (87%) than the NPV reported for tipifarnib monotherapy studies, which have been in the range of ~95%. This apparent discrepancy in NPV between single and combination therapies might relate, in part, to response to etoposide.

In summary, one skilled in the art will appreciate this disclosure is susceptible to many variations and alternative implementations without departing from its teachings or spirit. For instance, using an algebraic or mathematical variant of the two-gene ratio may be used to implement the method. The scope of the claims appended below includes many such modifications. Further, each reference discussed and cited herein is hereby incorporated herein by reference in its entirety.

---

SEQUENCES

RASGRP1 Amplicon SEQ ID NO: 1
ctggacgatctcattgacagctgcattcaatcttttgatgcagatggaaa
cctgtgtcgaagtaaccaactgttgcaag APTX Amplicon SEQ ID NO: 2
cgcttccgattgggctaccacgccattccgagtatgagccatgtacatct
tcatgtgatcagccaggattttgattct APTX UPPER PRIMER SEQ ID NO: 3
cgcttccgattgggctac APTX LOWER PRIMER SEQ ID NO: 4
agaatcaaaatcctggctgatc RASGRP1 UPPER PRIMER SEQ ID NO: 5
ctggacgatctcattgacagc RASGRP1 LOWER PRIMER SEQ ID NO: 6
cttgcaacagttggttacttcg, HMBS Amplicon SEQ ID NO: 7
cctgccactgtgcttcctcctggcttcaccatcggagccatctgcaagc
gggaaaaccctcatgat HMBS UPPER PRIMER SEQ ID NO: 8
cctgccactgtgcttcct HMBS LOWER PRIMER SEQ ID NO:9
atcatgagggttttcccgct RASGRP1 TAQMAN PROBE SEQ ID NO: 10
FAM-cattcaatcttttgatgcagatggaaacctg-BHQ1

APTX TAQMAN PROBE SEQ ID NO: 11
Gold 540-cacgccattccgagtatgagccatgtac-BHQ2

HMBS TaqMan probe, SEQ ID NO: 12
Cy5-gcttcaccatcggagccatctgca-BHQ1,

---

REFERENCES

Ahel et al. (2006) The neurodegenerative disease protein aprataxin resolves abortive DNA ligation intermediates Nature 443:713-716

Baylin et al. in Nature Clinical Practice (2005) 2:S1-S3

Bivona et al. (2003) Phospholipase Cgamma activates Ras on the Golgi apparatus by means of RasGRP1 Nature 424:694-698

Bos (1989) ras oncogenes in human cancer: a review Cancer Res 49:4682-4689

Bullinger et al. (2004) Use of gene-expression profiling to identify prognostic subclasses in adult acute myeloid leukemia N Engl J Med 350:1605-1616

Burger et al. (2005) Activating mutations in c-KIT and PDGFRalpha are exclusively found in gastrointestinal stromal tumors and not in other tumors overexpressing these imatinib mesylate target genes Cancer Biol Ther 4:1270-1274

Chang et al. (2003) Gene expression profiling for the prediction of therapeutic response to docetaxel in patients with breast cancer Lancet 362:362-369

Chen et al. (2005) FLT3/ITD mutation signaling includes suppression of SHP-1 J Biol Chem 280:5361-5369

Cox et al (2002) Farnesyltransferase inhibitors: promises and realities Curr Opin Pharmacol 2:388-393

Ebinu et al. (1998) RasGRP, a Ras guanyl nucleotide—releasing protein with calcium- and diacylglycerol-binding motifs Science 280:1082-1086

Ehmann et al. (2006) Detection of N-RAS and K-RAS in their active GTP-bound form in acute myeloid leukemia without activating RAS mutations Leuk Lymphoma 47:1387-1391

End et al. (2001) Characterization of the antitumor effects of the selective farnesyl protein transferase inhibitor R115777 in vivo and in vitro Cancer Res 61:131-137

Feldkamp et al. (2001) Isotype-specific RasGTP-levels predict the efficacy of farnesyl transferase inhibitors against human astrocytomas regardless of Ras mutational status Cancer Res 61:4425-4431

Geman et al. (2004) Classifying gene expression profiles from pairwise mRNA comparisons Stat Appl Genet Mol Biol 3:30

Holleman et al. (2004) Gene-expression patterns in drug-resistant acute lymphoblastic leukemia cells and response to treatment N Engl J Med 351:533-542

Illmer et al. (2005) Activation of the RAS pathway is predictive for a chemosensitive phenotype of acute myelogenous leukemia blasts Clin Cancer Res 11:3217-322

Jansen et al. (2005) Molecular classification of tamoxifen-resistant breast carcinomas by gene expression profiling J Clin Oncol 23:732-740

Karp et al. (2001) Clinical and biologic activity of the farnesyltransferase inhibitor R115777 in adults with refractory and relapsed acute leukemias: a phase 1 clinical-laboratory correlative trial Blood 97:3361-3369

Karp, Karen Flatten, Eric J. Feldman, Jacqueline M. Greer et al. Active oral regimen for elderly adults with newly diagnosed acute myelogenousleukemia: a preclinical and phase 1 trial of the farnesyltransferase inhibitor tipifarnib (R115777, Zarnestra) combined with etoposide. Blood 2009, 113:4841-4852.

Kawasaki et al. (1998) A Rap guanine nucleotide exchange factor enriched highly in the basal ganglia Proc Natl Acad Sci 95:13278-13283

Lancet et al. (2006) A phase II study of the farnesyltransferase inhibitor tipifarnib in poor-risk and elderly patients with previously untreated acute myelogenous leukemia Blood 2:2

Leith et al. Acute Myeloid Leukemia in the Elderly: Assessment of Multidrug Resistance (MDR1) and Cytogenetics Distinguishes Biologic Subgroups With Remarkably Distinct Responses to Standard Chemotherapy. A Southwest Oncology Group Study. Blood, Vol. 89, 1997: pp. 3323-3329.

Lossos et al. (2004) Prediction of survival in diffuse large-B-cell lymphoma based on the expression of six genes N Engl J Med 350:1828-1837

Lubet et al. (2006) Effects of the farnesyl transferase inhibitor R115777 (Zarnestra) on mammary carcinogenesis: prevention, therapy, and role of HaRas mutations Mol Cancer Ther 5:1073-1078

Lynch et al. (2004) Activating mutations in the epidermal growth factor receptor underlying responsiveness of non-small-cell lung cancer to gefitinib N Engl J Med 350: 2129-2139

Ma et al. (2004) A two-gene expression ratio predicts clinical outcome in breast cancer patients treated with tamoxifen Cancer Cell 5:607-616

Mesa et al (2006) Tipifarnib: farnesyl transferase inhibition at a crossroads Expert Rev Anticancer Ther 6:313-319

Moroni et al. (2005) Gene copy number for epidermal growth factor receptor (EGFR) and clinical response to antiEGFR treatment in colorectal cancer: a cohort study Lancet Oncol 6:279-286

Perez de Castro et al. (2004) A Ras activation in Jurkat T cells following low-grade stimulation of the T-cell receptor is specific to N-Ras and occurs only on the Golgi apparatus Mol Cell Biol 24:3485-3496

Potti et al. (2006) Genomic signatures to guide the use of chemotherapeutics Nat Med 12:1294-1300

Raponi M, Wang Y, and Hongtao F. WO2008112749 A1. Methods of determining acute myeloid leukemia response to treatment with farnesyltransferase.

Raponi M, Harousseau J L, Lancet J E, et al. Identification of molecular predictors of response in a study of tipifarnib treatment in relapsed and refractory acute myelogenous leukemia. Clin Cancer Res. 2007; 13: 2254-2260.

Raponi, Jeffrey E. Lancet, Hongtao Fan, Lesley Dossey, Grace Lee, Ivana Gojo, Eric J. Feldman, Jason Gotlib, Lawrence E. Morris, Peter L. Greenberg, John J. Wright, Jean-Luc Harousseau, Bob Lowenberg, Richard M. Stone, Peter De Porre, Yixin Wang, and Judith E. Karp. A 2-gene classifier for predicting response to the farnesyltransferase inhibitor tipifarnib in acute myeloid leukemia. Blood 2008, 111: 2589-2596.

Rao et al. (2004) Phase III Double-Blind Placebo-Controlled Study of Farnesyl Transferase Inhibitor R115777 in Patients With Refractory Advanced Colorectal Cancer J Clin Oncol 22:3950-3957

Reuter et al. (2000) Targeting the Ras signaling pathway: a rational, mechanism-based treatment for hematologic malignancies? Blood 96:1655-1669

Reuther et al. (2001) Leukemia-associated Rho guanine nucleotide exchange factor, a Dbl family protein found mutated in leukemia, causes transformation by activation of RhoA J Biol Chem 276:27145-27151

Reuther et al. (2002) RasGRP4 is a novel Ras activator isolated from acute myeloid leukemia J Biol Chem 277: 30508-30514

Rosenwald et al. (2002) The use of molecular profiling to predict survival after chemotherapy for diffuse large-B-cell lymphoma N Engl J Med 346:1937-1947

Rowinsky et al (1999) Ras protein farnesyltransferase: A strategic target for anticancer therapeutic development J Clin Oncol 17:3631-3652

Sahai et al. (2002) RHO-GTPases and cancer Nat Rev Cancer 2:133-142

Seidman et al. (2001) Weekly trastuzumab and paclitaxel therapy for metastatic breast cancer with analysis of efficacy by HER2 immunophenotype and gene amplification J Clin Oncol 19:2587-2595

Ship et al. (2002) Diffuse large B-cell lymphoma outcome prediction by gene-expression profiling and supervised machine learning Nat Med 8:68-74

Solit et al. (2006) BRAF mutation predicts sensitivity to MEK inhibition Nature 439:358-362

Sterpetti et al. (1999) Activation of the Lbc Rho exchange factor proto-oncogene by truncation of an extended C terminus that regulates transformation and targeting Mol Cell Biol 19:1334-1345

Stone (2006) Regulation of Ras in lymphocytes: get a GRP Biochem Soc Trans 34:858-861

Tognon et al. (1998) Regulation of RasGRP via a phorbol ester-responsive C1 domain Mol Cell Biol 18:6995-7008

Tsao et al. (2005) Erlotinib in lung cancer—molecular and clinical predictors of outcome N Engl J Med 353:133-144

Van Cutsem et al. (2004) Phase III trial of gemcitabine plus tipifarnib compared with gemcitabine plus placebo in advanced pancreatic cancer J Clin Oncol 22:1430-1438

Waters et al. (2006) Developing gene expression signatures of pathway deregulation in tumors Mol Cancer Ther 5:2444-2449

Weinstein et al. (2006) Mechanisms of disease: Oncogene addiction—a rationale for molecular targeting in cancer therapy Nat Clin Pract Oncol 3:448-457

White et al. (1997) K- and N-Ras are geranylgeranylated in cells treated with farnesyl protein transferase inhibitors J Biol Chem 272:14459-14464

Yeoh et al. (2002) Classification, subtype discovery, and prediction of outcome in pediatric acute lymphoblastic leukemia by gene expression profiling Cancer Cell 1:133-143.

The invention claimed is:

1. A method of treating a myeloid disorder in a patient, the method of treating comprising:
administering a therapeutically effective amount of tipifarnib and etoposide to a patient responsive to tipifarnib and etoposide and having a ratio of RASGRP1 and APTX expression levels that exceeds a ΔΔCt threshold, wherein said ΔΔCt threshold has been determined using a specified sensitivity or specificity or a maximized sum of sensitivity and specificity in a ROC analysis in a test population comprising tipifarnib- and etoposide-treated subjects, and wherein, prior to administering tipifarnib and etoposide to said patient, the ratio of RASGRP1 and APTX expression has been determined experimentally in a sample obtained from the patient using the ΔΔCt method and at least one primer selected from the group consisting of (i) 5'-CGCTTCCGATTGGGCTAC-3'   SEQ ID NO: 3

(ii) 5'-AGAATCAAAATCCTGGCTGATC-3'   SEQ ID NO: 4

(iii) 5'-CTGGACGATCTCATTGACAGC-3'   SEQ ID NO: 5
and

```
(iv)  5'-CTTGCAACAGTTGGTTACTTCG-3'.                SEQ ID NO: 6
```

2. The method of claim 1 wherein the ratio of RASGRP1 and APTX expression has been determined experimentally by using at least the following primers

```
(i)    5'-CGCTTCCGATTGGGCTAC-3'                    SEQ ID NO: 3

(ii)   5'-AGAATCAAAATCCTGGCTGATC-3'                SEQ ID NO: 4

(iii)  5'-CTGGACGATCTCATTGACAGC-3'                 SEQ ID NO: 5
and (iv)   5'-CTTGCAACAGTTGGTTACTTCG-3'.               SEQ ID NO: 6
```

3. The method of claim 1, wherein a level of expression of RASGRP1 is estimated relative to one or more genes selected from the group consisting of APTX, beta-actin, and HMBS.

4. The method of claim 1, wherein the ΔΔCt threshold has been determined using an area under the curve of 70% or more.

5. The method of claim 1, wherein the assay is performed in a single tube in a multiplex format.

6. The method of claim 2, wherein the ratio of expression levels of RASGRP1 relative to APTX has been determined using an external control.

7. The method of claim 6, wherein the external control is selected from the group consisting of one or more reference cell lines, JY RNA, Universal RNA, a standardized RNA reference and a reference patient sample.

8. The method of claim 1, wherein said ratio has been determined using a sample that comprises at least one of (i) a bone marrow sample; and (ii) a blood sample.

9. The method of claim 1, wherein the disorder is AML.

10. A method for administering tipifarnib and etoposide to a patient diagnosed with Acute Myelogenous Leukemia, the method comprising:

administering a therapeutically effective amount of tipifarnib and etoposide to a patient responsive to tipifarnib and etoposide, wherein said administration is effected after the patient's ratio of RASGRP1 and APTX expression levels has been determined to exceed a ΔΔCt threshold, wherein said threshold has been determined using a sensitivity or specificity or a maximized sum of sensitivity and specificity in a ROC analysis in a test population comprising tipifarnib- and etoposide-treated subjects, and wherein, prior to administering tipifarnib and etoposide to said patient, the patient's ratio of RASGRP1 and APTX expression has been determined experimentally in a sample obtained from the patient using the ΔΔCt method and at least one primer selected from the group consisting of

```
(i)    5'-CGCTTCCGATTGGGCTAC-3'                    SEQ ID NO: 3

(ii)   5'-AGAATCAAAATCCTGGCTGATC-3'                SEQ ID NO: 4

(iii)  5'-CTGGACGATCTCATTGACAGC-3'                 SEQ ID NO: 5
```
and
```
(iv)   5'-CTTGCAACAGTTGGTTACTTCG-3'.               SEQ ID NO: 6
```

11. The method of claim 10 wherein the ratio of RASGRP1 and APTX expression has been determined experimentally by using the ΔΔCt method and at least the following primers

```
(i)    5'-CGCTTCCGATTGGGCTAC-3'                    SEQ ID NO: 3

(ii)   5'-AGAATCAAAATCCTGGCTGATC-3'                SEQ ID NO: 4

(iii)  5'-CTGGACGATCTCATTGACAGC-3'                 SEQ ID NO: 5
and (iv)   5'-CTTGCAACAGTTGGTTACTTCG-3'.               SEQ ID NO: 6
```

12. The method of claim 10 wherein a level of expression of RASGRP1 is estimated relative to one or more of the group consisting of APTX, beta-actin and HMBS.

13. The method of claim 1, wherein the ΔΔCt threshold has been determined using an area under the curve of 70% or more.

14. The method of claim 10 wherein the assay is performed in a single tube in a multiplex format.

15. The method of claim 11 wherein the ratio of expression levels of RASGRP1 relative to APTX has been determined using an external control.

16. The method of claim 15, wherein the external control is selected from the group consisting of one or more reference cell lines, JY RNA, Universal RNA, a standardized RNA reference and a reference patient sample.

17. The method of claim 10, wherein said ratio has been determined using a sample that comprises at least one of (i) a bone marrow sample; and (ii) a blood sample.

18. The method of claim 10, wherein said patient diagnosed with Acute Myelogenous Leukemia is 55 years of age or older.

19. A method of treating a myeloid disorder in a patient, the method of treating comprising:

determining a ratio of RASGRP1 and APTX expression in a sample from the patient using the ΔΔCt method and at least one primer selected from the group consisting of

```
(i)    5'-CGCTTCCGATTGGGCTAC-3'                    SEQ ID NO: 3

(ii)   5'-AGAATCAAAATCCTGGCTGATC-3'                SEQ ID NO: 4

(iii)  5'-CTGGACGATCTCATTGACAGC-3'                 SEQ ID NO: 5
and (iv)   5'-CTTGCAACAGTTGGTTACTTCG-3',               SEQ ID NO: 6
```
and
subsequently administering a therapeutically effective amount of tipifarnib and etoposide to the patient having a ratio of RASGRP1 and APTX expression levels that exceeds a ΔΔCt threshold, wherein said ΔΔCt threshold has been determined using a specified sensitivity or specificity or a maximized sum of sensitivity and specificity in a ROC analysis in a test population comprising tipifarnib- and etoposide-treated subjects.

20. A method of treating a myeloid disorder in a patient having a ratio of RASGRP1 and APTX expression levels that exceeds a ΔΔCt threshold, the method of treating comprising:
   administering a therapeutically effective amount of tipifarnib and etoposide to said patient,
   wherein said ΔΔCt threshold has been determined using a specified sensitivity or specificity or a maximized sum of sensitivity and specificity in a ROC analysis in a test population,
   wherein, prior to administering tipifarnib and etoposide to said patient, the ratio of RASGRP1 and APTX expression has been determined experimentally in a sample obtained from the patient using the ΔΔCt method and at least one primer selected from the group consisting of (i)   5'-CGCTTCCGATTGGGCTAC-3'           SEQ ID NO: 3
   (ii)  5'-AGAATCAAAATCCTGGCTGATC-3'       SEQ ID NO: 4
   (iii) 5'-CTGGACGATCTCATTGACAGC-3'        SEQ ID NO: 5
   and
   (iv)  5'-CTTGCAACAGTTGGTTACTTCG-3',      SEQ ID NO: 6 and
   wherein the sample is a blood sample.

21. A method for administering tipifarnib and etoposide to a patient diagnosed with Acute Myelogenous Leukemia, the method comprising:
   administering a therapeutically effective amount of tipifarnib and etoposide to said patient,
   wherein said administration is effected after the patient's ratio of RASGRP1 and APTX expression levels has been determined to exceed a ΔΔCt threshold,
   wherein said threshold has been determined using a sensitivity or specificity or a maximized sum of sensitivity and specificity in a ROC analysis in a test population,
   wherein, prior to administering tipifarnib and etoposide to said patient, the patient's ratio of RASGRP1 and APTX expression has been determined experimentally in a sample obtained from the patient using the ΔΔCt method and at least one primer selected from the group consisting of (i)   5'-CGCTTCCGATTGGGCTAC-3'           SEQ ID NO: 3
   (ii)  5'-AGAATCAAAATCCTGGCTGATC-3'       SEQ ID NO: 4
   (iii) 5'-CTGGACGATCTCATTGACAGC-3'        SEQ ID NO: 5
   and
   (iv)  5'-CTTGCAACAGTTGGTTACTTCG-3',      SEQ ID NO: 6 and
   wherein the sample is a blood sample.

22. A method of treating a myeloid disorder in a patient having a ratio of RASGRP1 and APTX expression levels that exceeds a ΔΔCt threshold, the method of treating comprising:
   determining the ratio of RASGRP1 and APTX expression using the ΔΔCt method and at least one primer selected from the group consisting of (i)   5'-CGCTTCCGATTGGGCTAC-3'           SEQ ID NO: 3
   (ii)  5'-AGAATCAAAATCCTGGCTGATC-3'       SEQ ID NO: 4
   (iii) 5'-CTGGACGATCTCATTGACAGC-3'        SEQ ID NO: 5
   and
   (iv)  5'-CTTGCAACAGTTGGTTACTTCG-3',      SEQ ID NO: 6 and
   subsequently administering a therapeutically effective amount of tipifarnib and etoposide to said patient,
   wherein said ΔΔCt threshold has been determined using a specified sensitivity or specificity or a maximized sum of sensitivity and specificity in a ROC analysis in a test population, and
   wherein the ratio of RASGRP1 and APTX expression levels is determined by using a blood sample of said patient.

23. The method of claim 1 wherein the ratio of RASGRP1 and APTX expression has been determined experimentally in a sample obtained from the patient using the ΔΔCt method according to equation 1:

$$\text{RASGRP1:APTX ratio} = 2^{-((A-B)-(C-D))} \qquad \text{Equation 1,}$$

where:
A: Sample RasGRP1 Ct value,
B: JY (or Universal) RNA (+) RASGRP1 Ct value,
C: Sample APTX Ct Value, and
D: JY (or Universal) RNA (+) APTX Ct Value.

24. The method of claim 1, wherein treating comprises administering the therapeutically effective amount of tipifarnib and etoposide to patients in a patient population responsive to tipifarnib and etoposide and having a ratio of RASGRP1 and APTX expression levels that exceeds a ΔΔCt threshold, and
detecting a response to the therapeutically effective amount of tipifarnib and etoposide in greater than 50% of the patients in the patient population.

* * * * *